US009956531B2

(12) United States Patent
Dacey, Jr. et al.

(10) Patent No.: US 9,956,531 B2
(45) Date of Patent: May 1, 2018

(54) DEVICE INCLUDING MULTILAYER MEMBRANE TO CONTROL FLUID DRAINAGE AND METHODS OF USE THEREOF

(71) Applicant: Elwha LLC, Bellevue, WA (US)

(72) Inventors: Ralph G. Dacey, Jr., St. Louis, MO (US); Roderick A. Hyde, Redmond, WA (US); Muriel Y. Ishikawa, Livermore, CA (US); Jordin T. Kare, San Jose, CA (US); Eric C. Leuthardt, St. Louis, MO (US); Nathan P. Myhrvold, Medina, WA (US); Dennis J. Rivet, Chesapeake, VA (US); Michael A. Smith, Phoenix, AZ (US); Clarence T. Tegreene, Mercer Island, WA (US); Lowell L. Wood, Jr., Bellevue, WA (US); Victoria Y. H. Wood, Livermore, CA (US)

(73) Assignee: Elwha LLC, Bellevue, WA (US)

( * ) Notice: Subject to any disclaimer, the term of this patent is extended or adjusted under 35 U.S.C. 154(b) by 520 days.

(21) Appl. No.: 14/593,110

(22) Filed: Jan. 9, 2015

(65) Prior Publication Data
US 2016/0199561 A1 Jul. 14, 2016

(51) Int. Cl.
*B01D 69/00* (2006.01)
*B01D 69/06* (2006.01)
(Continued)

(52) U.S. Cl.
CPC ....... *B01D 67/0088* (2013.01); *A61M 1/0088* (2013.01); *A61M 1/1623* (2014.02);
(Continued)

(58) Field of Classification Search
CPC .................................................. A61M 1/1623
See application file for complete search history.

(56) References Cited

U.S. PATENT DOCUMENTS 6,459,957 B1 10/2002 Bennett, III et al.
6,545,391 B1 4/2003 Su et al.
(Continued)

FOREIGN PATENT DOCUMENTS

WO    WO 2014207430 A1 * 12/2014  ......... C01B 31/0253

OTHER PUBLICATIONS

Bhimani et al.; "Effect of increasing dialysate flow rate on diffusive mass transfer of area, phosphate and $\beta_2$-microglobulin during clinical haemodialysis"; Nephrol Dial Transplant; Jun. 13, 2010; pp. 3990-3995; vol. 25.
(Continued)

*Primary Examiner* — Krishnan S Menon
*Assistant Examiner* — Bradley R Spies

(57) ABSTRACT

A device and methods are disclosed herein for fluid removal during wound treatment or for removal or dialysis of components from blood or tissue. A device is disclosed that includes a multilayer membrane including a plurality of layers; an electroactive polymer within each layer; and a controller operably connected to sequentially activate the electroactive polymer to alter one or more sizes of the plurality of the variably-sized pores within one or more layers of the multilayer membrane. A device is disclosed that includes a multilayer membrane including a plurality of layers; an actuator operably attached to the plurality of layers of the multilayer membrane; and a controller operably activating the actuator to alter a relative lateral position of the two or more layers of the multilayer membrane to align two or more of the plurality of pores within the plurality of layers of the multilayer membrane.

46 Claims, 8 Drawing Sheets

(51) Int. Cl.
| | | |
|---|---|---|
| A61M 1/16 | (2006.01) | |
| A61M 1/20 | (2006.01) | |
| A61M 1/26 | (2006.01) | |
| B01D 67/00 | (2006.01) | |
| A61M 1/00 | (2006.01) | |
| B01D 69/12 | (2006.01) | |

(52) U.S. Cl.
CPC ........... *A61M 1/1631* (2014.02); *B01D 69/12* (2013.01); *A61M 2205/3334* (2013.01); *B01D 2325/26* (2013.01)

(56) References Cited

U.S. PATENT DOCUMENTS

| | | | |
|---|---|---|---|
| 6,724,130 | B1 | 4/2004 | Su et al. |
| 7,015,624 | B1 | 3/2006 | Su et al. |
| 7,632,406 | B2 | 12/2009 | Wilson et al. |
| 2002/0152006 | A1 | 10/2002 | Bennett, III et al. |
| 2005/0016915 | A1* | 1/2005 | Beck .................. D21F 3/0272 210/490 |
| 2006/0138371 | A1 | 6/2006 | Garnier |
| 2008/0243082 | A1 | 10/2008 | Goodman |
| 2010/0298790 | A1 | 11/2010 | Guidi et al. |
| 2016/0368771 | A1* | 12/2016 | White .................. C01B 31/0266 |

OTHER PUBLICATIONS

Burns et al.; "Lipid-Bilayer-Spanning DNA Nanopores with a Bifunctional Porphyrin Anchor"; Angewandte Chemie International Edition, vol. 52, Issue 46, p. 11943, Abstract only (4 pages total); Nov. 11, 2013.

Chen et al.; "Continuous wireless pressure monitoring and mapping with ultra-small passive sensors for health monitoring and critical care"; Nature Communications; Oct. 6, 2014; pp. 1-10; MacMillan Publishers Limited.

Crystal IS SMD UVC LEDs; Technical Data Sheet; bearing a date of Apr. 3, 2014; 8 pages.

Electro-active Polymers and Their Applications; University of Washington; UW—Center for Intelligent Materials and Systems; five pages; downloaded on Jan. 5, 2015.

Isildak et al.; "A novel conductometric creatinine biosensor based on solid-state contact ammonium sensitive PVC-$NH_2$ membrane"; Biochemical Engineering Journal; available online Dec. 8, 2011; pp. 34-38; vol. 62; Elsevier B.V.

Jeong et al.; "Fabrication of a peristaltic PDMS micropump"; Sensors and Actuators A; available online Feb. 23, 2005; pp. 453-458; vols. 123-124; Elsevier B.V.

Laurinavicius et al.; "Bioelectrochemical Conversion of Urea on Carbon Black Electrode and Application"; IEEE Sensors Journal; Jun. 2013; pp. 2208-2213; vol. 13, No. 6; IEEE.

McColl et al.; "Monitoring moisture without disturbing the wound dressing"; Wounds UK; bearing a date of 2009; pp. 94-99; vol. 5, No. 3.

PL0xx PICMA® Chip Actuators product infoimation; printed on Oct. 15, 2014; pp. 1-3; located at piceramic.com/product-detail-page/p10xx-100800.html.

Price et al.; "Development of membrane systems based on conducting polymers"; Synthetic Metals; bearing a date of 1999; pp. 1338-1341; vol. 102; Elsevier Science S.A.

ReadyCircuit™ bags and tubing assemblies; GE Conductivity Sensor Spec; Data file 28-9606-44 AF;GE; bearing a date of May 2014; 16 pages; located at www.gelifesciences.com/readytoprocess.

Pore Sizes for Ultrafiltration, Microfiltration, Dyalysis, and Macrofiltration at Spectrum Labs; Pore Size Chart, one page, printed on Jan. 8, 2015; located at www.spectrumlabs.com/filtration/PoreSize.html.

Shkolnikov et al; "A self-priming, roller-free, miniature, peristaltic pump operable with a single, reciprocating actuator"; Sensors and Actuators A: Physical; available online May 5, 2010; pp. 141-146; vol. 160; Elsevier B.V.

Stroeve et al.; "Biotechnical and other applications of nanoporous membranes"; Trends in Biotechnology; TIBTEC-879; published online Mar. 8, 2011; pp. 1-8; Elsevier Ltd.

The PTFE Story; Jan. 10, 2014; product information; two pages; located at www.gore.com/en.xx/technology/index.hml; W. L. Gore & Associates.

Uchino, Kenji; "Piezoelectric and Electrostrictive Actuators"; pp. 610-618; downloaded on Dec. 18, 2014; IEEE 1986.

Wikol et al.; "Expanded Polytetrafluoroethylene Membranes and Their Applications"; Filtration and Purification in the Biopharmaceutical Industry, Second Edition; 2008; cover page; pp. 619-640.

White et al.; World Wide Wounds; "Modern exudate management: a review of wound treatments"; 2006; pp. 1-6; available online at: http://www.worldwidewounds.com/2006/september/White/Modern-Exudate-Mgt.html; printed Oct. 14, 2014.

\* cited by examiner

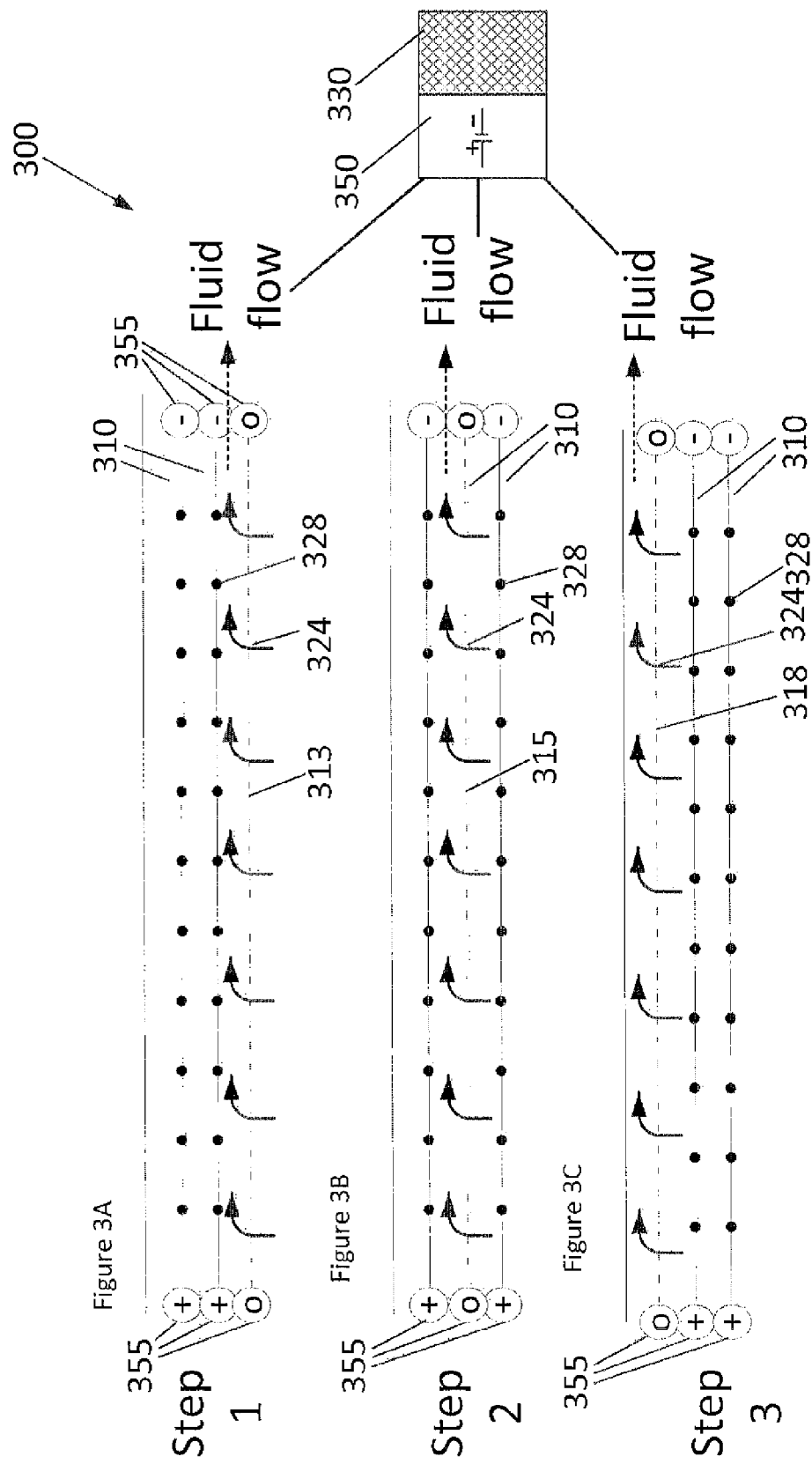

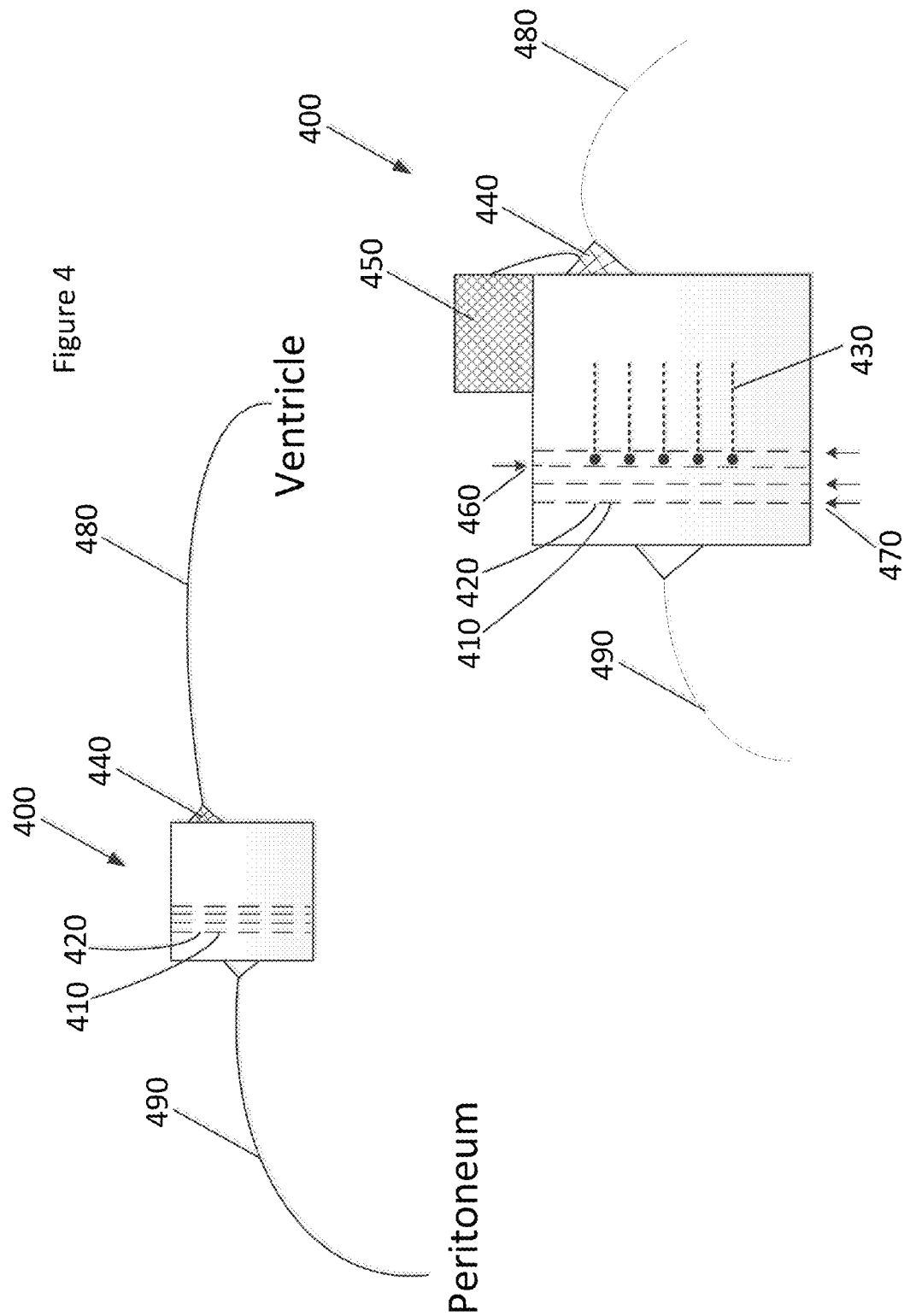

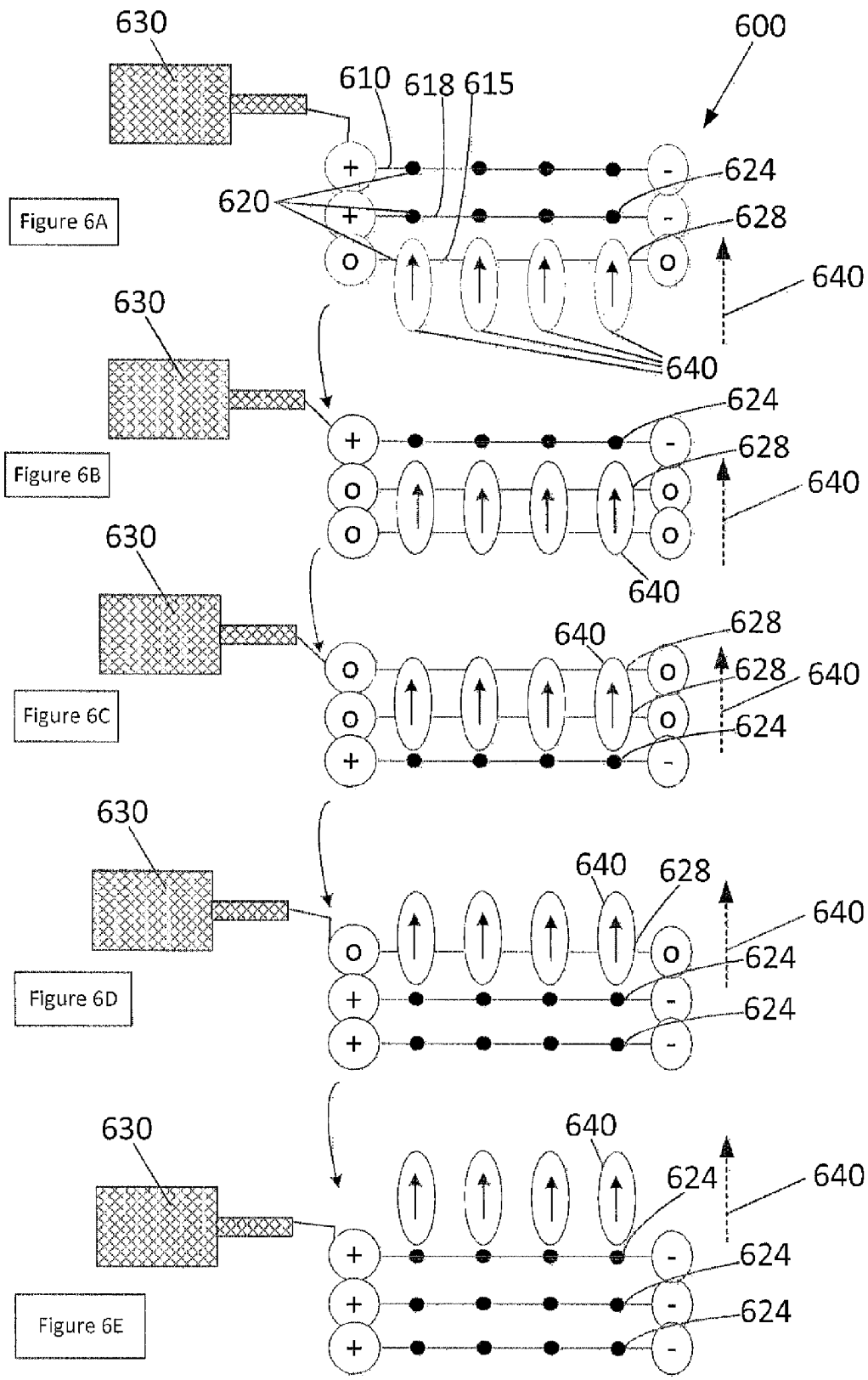

DEVICE INCLUDING MULTILAYER MEMBRANE TO CONTROL FLUID DRAINAGE AND METHODS OF USE THEREOF

If an Application Data Sheet (ADS) has been filed on the filing date of this application, it is incorporated by reference herein. Any applications claimed on the ADS for priority under 35 U.S.C. § § 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc, applications of the Priority Application(s)).

PRIORITY APPLICATIONS

None.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

A device and methods of use thereof are disclosed herein for fluid removal during wound treatment or for removal or dialysis of components from blood or tissue. A device is disclosed that includes: a multilayer membrane including a plurality of layers, each layer of the plurality of layers having a plurality of variably-sized pores; an electroactive polymer within the each layer and surrounding each of the plurality of variably-sized pores; and a controller operably connected to sequentially activate the electroactive polymer to alter one or more sizes of the plurality of the variably-sized pores within a first layer of the multilayer membrane and to sequentially alter one or more sizes of the variably-sized pores sequentially within a second layer and one or more subsequent layers of the multilayer membrane; wherein at least one of the plurality of the variably-sized pores in the first layer is aligned with at least one of the plurality of variably-sized pores in one or more subsequent layers of the multilayer membrane.

In some aspects, the controller sequentially activates the electroactive polymer to vary aperture of one or more of the plurality of the variably-sized pores and to vary accessibility to the one or more of the plurality of the variably-sized pores within the multilayer membrane. The controller may be responsive to a conditional stimulus. In some aspects of the device, the at least one of the plurality of the variably-sized pores in the first layer aligned with the at least one of the plurality of variably-sized pores in one or more subsequent layers of the multilayer membrane are accessible to fluid flow through a plurality of layers of the multilayer membrane in response to the conditional stimulus. The conditional stimulus may include one or more of pH stimulus, chemical stimulus, analyte stimulus, fluid presence stimulus, electrical stimulus, magnetic stimulus, or pressure stimulus. The conditional stimulus may include one or more of programmed stimulus, scheduled stimulus, open loop pulsed stimulus, or stimulus provided by an external command.

In some aspects, the controller may be operably connected to activate the electroactive polymer in the plurality of layers of the multilayer membrane to produce peristaltic pumping activity by aligned variably-sized pores in three or more layers of the multilayer membrane. The controller may be operably connected to activate the electroactive polymer to alter the size of one or more aligned variably-sized pores sequentially for each layer of two or more layers of the multilayer membrane to generate pressure or suction through the multilayer membrane. The controller may be operably connected to activate the electro active polymer in to provide variable fluid flow rates by separately controlling the size of one or more aligned variably-sized pores of each layer of two or more layers of the multilayer membrane. The device of claim 1, wherein the controller may be operably connected to activate the electroactive polymer to separately control movement of each layer of two or more layers to provide variable fluid flow rates. In some aspects of the device, a pump may be configured to apply pressure or suction to the multilayer membrane. The controller may be operably connected to alter the relative position of the two or more layers of the multilayered membranes to expose one or more of the plurality of variably-sized pores in each of the two or more layers to pressure or suction from the pump.

In some aspects, the controller may be operably connected to activate the electroactive polymer to push fluid flow or pull fluid flow through each layer of the two or more layers of the multilayer membrane. The controller may be operably connected to activate the electroactive polymer to provide pulsed transport of fluid to control entry rate and exit rate of fluid through the multilayered membrane. The controller may be operably connected to activate the electroactive polymer to provide continuous transport to control entry rate and exit rate of fluid through the multilayered membrane. In some aspects, the device may include one or more nanoporous layers in the multilayer membrane, wherein the controller is operably connected to activate the electroactive polymer in the one or more nanoporous layers to provide controlled transport of fluid through the one or more nanoporous layers. The device may include one or more of a surgical drainage device, CSF shunt, or an artificial kidney. The device may include a UV illumination source to provide self-sterilization of the device. The controller may be external to the device. The controller may include operational programs for self-cleaning the device.

A method of varying a fluid flow rate through a multilayer membrane is disclosed that includes: sending a control signal from a controller operably connected to activate an electroactive polymer within each layer of a plurality of layers of a multilayer membrane, wherein the electroactive polymer surrounds each of a plurality of variably-sized pores in the plurality of layers of the multilayer membrane;

altering the electroactive polymer surrounding one or more sizes of the plurality of variably-sized pores within a first layer of the multilayer membrane and altering the one or more sizes of the variably-sized pores sequentially within a second layer and one or more subsequent layers of the multilayer membrane; and aligning at least one of the plurality of the variably-sized pores in the first layer with at least one of the plurality of variably-sized pores in one or more subsequent layers of the multilayer membrane.

The method may include: controlling accessibility to the one or more sizes of the plurality of the variably-sized pores within the multilayer membrane by altering the electroactive polymer in response to a conditional stimulus. The method may include: receiving a conditional stimulus at the controller. The method may further include: aligning the at least one of the plurality of the variably-sized pores in the first layer with the at least one of the plurality of variably-sized pores in one or more subsequent layers of the multilayer membrane to provide access to fluid flow through a plurality of layers of the multilayer membrane in response to the conditional stimulus. The method may include: sending a control signal from the controller operably connected to activate the electroactive polymer in the plurality of layers of the multilayer membrane to produce peristaltic pumping activity by aligned variably-sized pores in three or more layers of the multilayer membrane. The method may further include: sending a control signal from the controller operably connected to activate the electroactive polymer to alter the size of one or more aligned variably-sized pores sequentially for each layer of two or more layers of the multilayer membrane to generate pressure or suction through the multilayer membrane.

The method may include: sending a control signal from the controller operably connected to activate the electroactive polymer to provide variable fluid flow rates by separately controlling the size of one or more aligned variably-sized pores of each layer of two or more layers of the multilayer membrane. The method may include: sending a control signal from the controller operably connected to activate the electroactive polymer to separately control movement of each layer of two or more layers to provide variable fluid flow rates. The method may include: applying pressure or suction to the multilayer membrane through a pump. The method may further include: sending a control signal from the controller to alter the relative position of two or more layers of the multilayered membranes to expose the one or more of the plurality of variably-sized pores in each of the two or more layers to pressure or suction from the pump. The method may include: sending a control signal from the controller to control fluid flow through each layer of the plurality of layers of the multilayer membrane by altering the electroactive polymer to push fluid flow or pull fluid flow through the multilayer membrane. The method may include: sending a control signal from the controller to control fluid flow through each layer of the plurality of layers of the multilayer membrane by altering the electroactive polymer to provide pulsed transport to control entry rate and exit rate of fluid through the multilayered membrane. The method may include: sending a control signal from the controller to control fluid flow through each layer of the plurality of layers of the multilayer membrane by altering the electroactive polymer to provide continuous transport to control entry rate and exit rate of fluid through the multilayered membrane. The method may include: sending a control signal from the controller to alter the electroactive polymer in one or more nanoporous layers of the plurality of layers of the multilayer membrane to control flow through the one or more nanoporous layers. The method may include: sending a control signal from the controller to a UV illumination source to activate self-sterilization of the device.

A method is disclosed that includes: providing a multilayer membrane including a plurality of layers, each layer of the plurality of layers having an electroactive polymer, wherein the electroactive polymer surrounds each of a plurality of variably-sized pores in the plurality of layers of the multilayer membrane; sequentially activating the electroactive polymer by a controller operably connected to activate the electroactive polymer and to alter one or more sizes of the plurality of variably-sized pores within a first layer of the multilayer membrane and altering one or more sizes of the variably-sized pores sequentially within a second layer and one or more subsequent layers of the multilayer membrane; and aligning at least one of the plurality of the variably-sized pores in the first layer with at least one of the plurality of variably-sized pores in one or more subsequent layers of the multilayer membrane.

A device is disclosed that includes: a multilayer membrane including a plurality of layers, each layer of the plurality of layers having a plurality of pores on the plurality of layers of the multilayer membrane; an actuator operably attached to the plurality of layers of the multilayer membrane; and a controller operably activating the actuator to alter a relative lateral position of two or more layers of the plurality of layers to align two or more of the plurality of pores within the two or more layers of the plurality of layers of the multilayer membrane; wherein the two or more pores are aligned and accessible through the two or more layers of the plurality of layers of the multilayer membrane. In some aspects, two or more pores of the each layer of the plurality of layers have a substantially identical size. The two or more pores of the substantially identically-sized pores may be aligned and accessible through the plurality layers of the multilayer membrane. In some aspects of the device, at least one pore of the each layer of the plurality of layers have a variable size. The controller may be operably connected to alter the size of the variably-sized pores.

In some aspects, the controller may be operably connected to the plurality of layers of the multilayer membrane to produce peristaltic pumping activity by aligned variably-sized pores in three or more layers of the multilayer membrane. The controller may be operably connected to alter the size of at least one aligned variably-sized pores of each layer of the two or more layers to generate pressure or suction. The controller may be operably connected to provide variable flow rates by separately controlling the size of the aligned variably-sized pores of the each layer of the two or more layers. The controller may be operably connected to sequentially activate the actuator to vary accessibility to the two or more of the plurality of pores. The controller may be responsive to a conditional stimulus. In some aspects, the conditional stimulus may include one or more of pH stimulus, chemical stimulus, analyte stimulus, fluid presence stimulus, electrical stimulus, magnetic stimulus, or pressure stimulus. In some aspects, the conditional stimulus may include one or more of programmed stimulus, scheduled stimulus, open loop pulsed stimulus, or stimulus provided by an external command. The plurality of pores may include pores of variable size and pores of fixed size. The device may further include a pump configured to apply pressure or suction to the multilayer membrane.

In some aspects of the device, the controller operably may activate the actuator to alter the relative position of the two or more layers of the multilayered membranes to expose one or more of the plurality of pores to pressure or suction from the pump. In some aspects, the controller may operably activate the actuator to provide variable fluid flow rates by separately controlling lateral movement of each layer of the two or more layers. The controller may operably activate the actuator to alter the relative lateral position of the two or more layers of the plurality of layers to push fluid flow or pull fluid flow through each layer of the two or more layers of the plurality of layers. The controller may provide pulsed signals to the actuator to control entry rate and exit rate of fluid through the multilayered membrane. The controller operably may activate the actuator to initiate continuous transport to control entry rate and exit rate of fluid through the multilayered membrane. In some aspects, the device may include one or more nanoporous layers in the multilayer membrane, wherein the controller operably activates the actuator to open and close pores to provide controlled transport of fluid through the nanoporous layer. In some aspects, the device may include one or more of a surgical drainage device, CSF shunt, or an artificial kidney. The device may further include a UV illumination source to provide self-sterilization of the device. In some aspects, the controller is external to the device. In some aspects, the controller includes operational programs for self-cleaning the device.

A method of varying a fluid flow rate through a multilayer membrane is disclosed that includes: sending a control signal from a controller operably connected to activate an actuator operably attached to a plurality of layers of the multilayer membrane to alter a relative lateral position of two or more layers of the plurality of layers, wherein each layer of the plurality of layers has a plurality of pores on the plurality of layers; and aligning by the actuator two or more pores of the plurality of pores in the two or more layers of the multilayer membrane.

The method may include: controlling accessibility to the two or more pores within the multilayer membrane by activating the actuator to align the two or more pores of the plurality of pores. The method may include: receiving a conditional stimulus at the controller. The method may include: sending a control signal from the controller to activate the actuator to alter the relative lateral position of three or more layers of the multilayer membrane to produce peristaltic pumping activity by aligned pores in the three or more layers. The method may further include: applying pressure or suction to the multilayer membrane through a pump. The method may include: sending a control signal from the controller to alter the relative position of two or more layers of the multilayered membranes to expose the two or more pores to pressure or suction from the pump.

The method may include: sending a control signal from the controller to control fluid flow through each layer of the two or more layers of the multilayer membrane by activating the actuator to push flow or pull flow through the multilayer membrane. The method may include: sending a control signal from the controller to control fluid flow through each layer of the two or more layers of the multilayer membrane by activating the actuator to provide pulsed transport to control entry rate and exit rate of fluid through the multilayered membrane. The method may include: sending a control signal from the controller to control fluid flow through each layer of the two or more layers of the multilayer membrane by activating the actuator to control continuous transport to control entry rate and exit rate of fluid through the multilayer membrane. The method may include: sending a control signal from the controller to control fluid flow through each layer of the two or more layers of the multilayer membrane by activating the actuator to control flow through one or more nanoporous layers in the multilayer membrane. The method may include: sending a control signal from the controller to a UV illumination source to activate self-sterilization of the device.

A method is disclosed that includes: providing a multilayer membrane including a plurality of layers, each layer of the plurality of layers having a plurality of pores on the plurality of layers of the multilayer membrane; operably activating an actuator by a controller to alter a relative lateral position of two or more layers of the plurality of layers; and aligning by the actuator two or more pores of the plurality of pores in the two or more layers of the multilayer membrane.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 3A, 3B, and 3C depict a diagrammatic view of an aspect of a device.

FIG. 4 depicts a diagrammatic view of an aspect of a device.

FIGS. 6A, 6B, 6C, 6D, and 6E depict a diagrammatic view of an aspect of a device.

DETAILED DESCRIPTION

Figure 1:
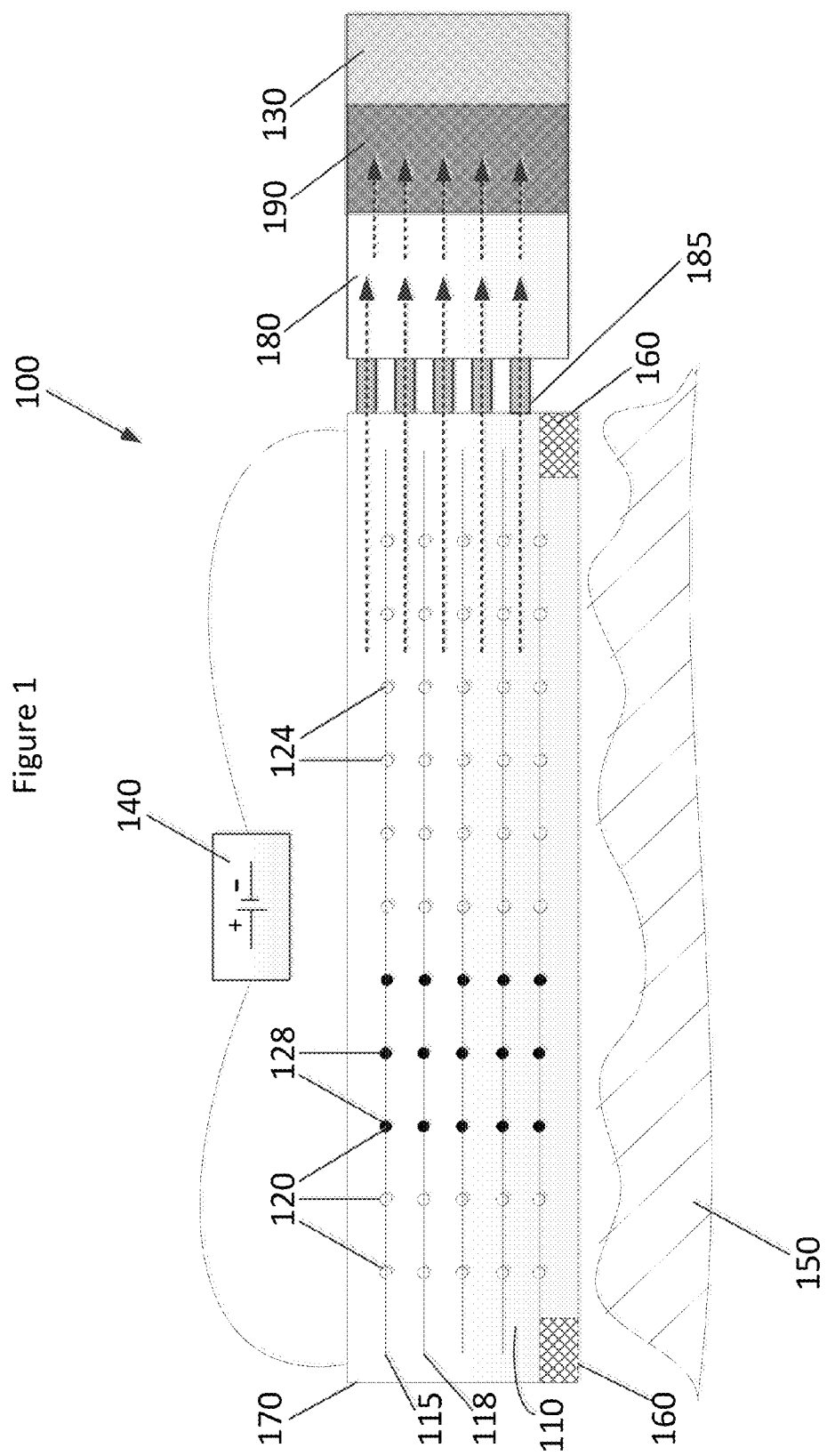
FIG. 1 depicts a diagrammatic view of an aspect of a device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

A device and methods of use thereof are disclosed herein for fluid removal during wound treatment or for removal or dialysis of components from blood or tissue. A device is disclosed that includes: a multilayer membrane including a plurality of layers, each layer of the plurality of layers having a plurality of variably-sized pores; an electroactive polymer within the each layer and surrounding each of the plurality of variably-sized pores; and a controller operably connected to sequentially activate the electroactive polymer to alter one or more sizes of the plurality of the variably-sized pores within a first layer of the multilayer membrane and to sequentially alter one or more sizes of the variably-sized pores sequentially within a second layer and one or more subsequent layers of the multilayer membrane; wherein at least one of the plurality of the variably-sized pores in the first layer is aligned with at least one of the plurality of variably-sized pores in one or more subsequent layers of the multilayer membrane.

In some aspects, the controller may sequentially activate the electroactive polymer to vary aperture of one or more of the plurality of the variably-sized pores and to vary accessibility to the one or more of the plurality of the variably-sized pores within the multilayer membrane. The controller may be responsive to a conditional stimulus. In some aspects of the device, the at least one of the plurality of the variably-sized pores in the first layer aligned with the at least one of the plurality of variably-sized pores in one or more subsequent layers of the multilayer membrane are accessible to fluid flow through a plurality of layers of the multilayer membrane in response to the conditional stimulus. In some aspects of the device, the controller may be operably connected to activate the electroactive polymer in the plurality of layers of the multilayer membrane to produce peristaltic pumping activity by aligned variably-sized pores in three or more layers of the multilayer membrane. The controller may be operably connected to activate the electroactive polymer to alter the size of one or more aligned variably-sized pores sequentially for each layer of two or more layers of the multilayer membrane to generate pressure or suction through the multilayer membrane.

A method of varying a fluid flow rate through a multilayer membrane is disclosed that includes: sending a control signal from a controller operably connected to activate an electroactive polymer within each layer of a plurality of layers of a multilayer membrane, wherein the electroactive polymer surrounds each of a plurality of variably-sized pores in the plurality of layers of the multilayer membrane; altering the electroactive polymer surrounding one or more sizes of the plurality of variably-sized pores within a first layer of the multilayer membrane and altering the one or more sizes of the variably-sized pores sequentially within a second layer and one or more subsequent layers of the multilayer membrane; and aligning at least one of the plurality of the variably-sized pores in the first layer with at least one of the plurality of variably-sized pores in one or more subsequent layers of the multilayer membrane.

A method is disclosed that includes: providing a multilayer membrane including a plurality of layers, each layer of the plurality of layers having an electroactive polymer, wherein the electroactive polymer surrounds each of a plurality of variably-sized pores in the plurality of layers of the multilayer membrane; sequentially activating the electroactive polymer by a controller operably connected to activate the electroactive polymer and to alter one or more sizes of the plurality of variably-sized pores within a first layer of the multilayer membrane and altering one or more sizes of the variably-sized pores sequentially within a second layer and one or more subsequent layers of the multilayer membrane; and aligning at least one of the plurality of the variably-sized pores in the first layer with at least one of the plurality of variably-sized pores in one or more subsequent layers of the multilayer membrane.

A device is disclosed that includes: a multilayer membrane including a plurality of layers, each layer of the plurality of layers having a plurality of pores on the plurality of layers of the multilayer membrane; an actuator operably attached to the plurality of layers of the multilayer membrane; and a controller operably activating the actuator to alter a relative lateral position of two or more layers of the plurality of layers to align two or more of the plurality of pores within the two or more layers of the plurality of layers of the multilayer membrane; wherein the two or more pores are aligned and accessible through the two or more layers of the plurality of layers of the multilayer membrane. In some aspects, two or more pores of the each layer of the plurality of layers have a substantially identical size. The two or more pores of the substantially identically-sized pores may be aligned and accessible through the plurality layers of the multilayer membrane. In some aspects of the device, at least one pore of the each layer of the plurality of layers have a variable size. The controller may be operably connected to alter the size of the variably-sized pores.

In some aspects, the controller may be operably connected to the plurality of layers of the multilayer membrane to produce peristaltic pumping activity by aligned variably-sized pores in three or more layers of the multilayer membrane. The controller may be operably connected to alter the size of at least one aligned variably-sized pores of each layer of the two or more layers to generate pressure or suction. The controller may be operably connected to provide variable flow rates by separately controlling the size of the aligned variably-sized pores of the each layer of the two or more layers.

A method of varying a fluid flow rate through a multilayer membrane is disclosed that includes: sending a control signal from a controller operably connected to activate an actuator operably attached to a plurality of layers of the multilayer membrane to alter a relative lateral position of two or more layers of the plurality of layers, wherein each layer of the plurality of layers has a plurality of pores on the plurality of layers; and aligning by the actuator two or more pores of the plurality of pores in the two or more layers of the multilayer membrane.

A method is disclosed that includes: providing a multilayer membrane including a plurality of layers, each layer of the plurality of layers having a plurality of pores on the plurality of layers of the multilayer membrane; operably activating an actuator by a controller to alter a relative lateral position of two or more layers of the plurality of layers; and aligning by the actuator two or more pores of the plurality of pores in the two or more layers of the multilayer membrane.

FIG. 1 depicts a diagrammatic view of an aspect of a device. A device 100 may be placed upon a wound 150 of a mammalian subject to draw liquid from the wound 150 and through a plurality of variably-sized pores 120 of the device 100. The device 100 includes a sealant 160 to seal the device including a shell 170 around the device to surround the wound 150 of the mammalian subject. A device 100 comprising: a multilayer membrane 110 including a plurality of layers 115, 118, each layer of the plurality of layers having a plurality of variably-sized pores 120; an electroactive polymer 124, 128 within the each layer 115, 118 and surrounding each of the plurality of variably-sized pores 120; and a controller 130 operably connected to sequentially activate the electroactive polymer 124, 128 to alter one or more sizes of the plurality of the variably-sized pores 120 within a first layer 115 of the multilayer membrane and to sequentially alter one or more sizes of the variably-sized pores 120 sequentially within a second layer 118 and one or more subsequent layers 118 of the multilayer membrane 110; wherein at least one of the plurality of the variably-sized pores 120 in the first layer 115 is aligned with at least one of the plurality of variably-sized pores in one or more subsequent layers 118 of the multilayer membrane 110. The variably-sized pores 120 may be opened 124 or closed 128 in response to the conditional stimulus. The controller 130 may be configured to respond to the conditional stimulus by varying accessibility to the one or more of the plurality of the variably-sized pores 120 within the multilayer membrane 110. The device 100 includes the controller 130 and circuitry including a battery 140 is used to draw an electrical potential across each membrane layer 110.

A pump 180 (e.g., a peristaltic pump, a MEMS pump, a micro-vibrating flow pump, or a micropump) is operably attached to the device through compartmental outlets 185 into a holding reservoir 190. The pump 180 is configured to apply pressure or suction to the device including the multilayer membrane 110 to draw liquid out of the wound and through the pores 120 of the device. In some aspects in addition to or instead of the pump attached to the device, the controller may sequentially activate the electroactive polymer to vary aperture of one or more of the plurality of the variably-sized pores and to vary accessibility to the one or more of the plurality of the variably-sized pores within the multilayer membrane in response to the conditional stimulus. The controller may be operably connected to activate the electroactive polymer in the plurality of layers of the multilayer membrane to produce peristaltic pumping activity by aligned variably-sized pores in three or more layers of the multilayer membrane.

Figure 2:
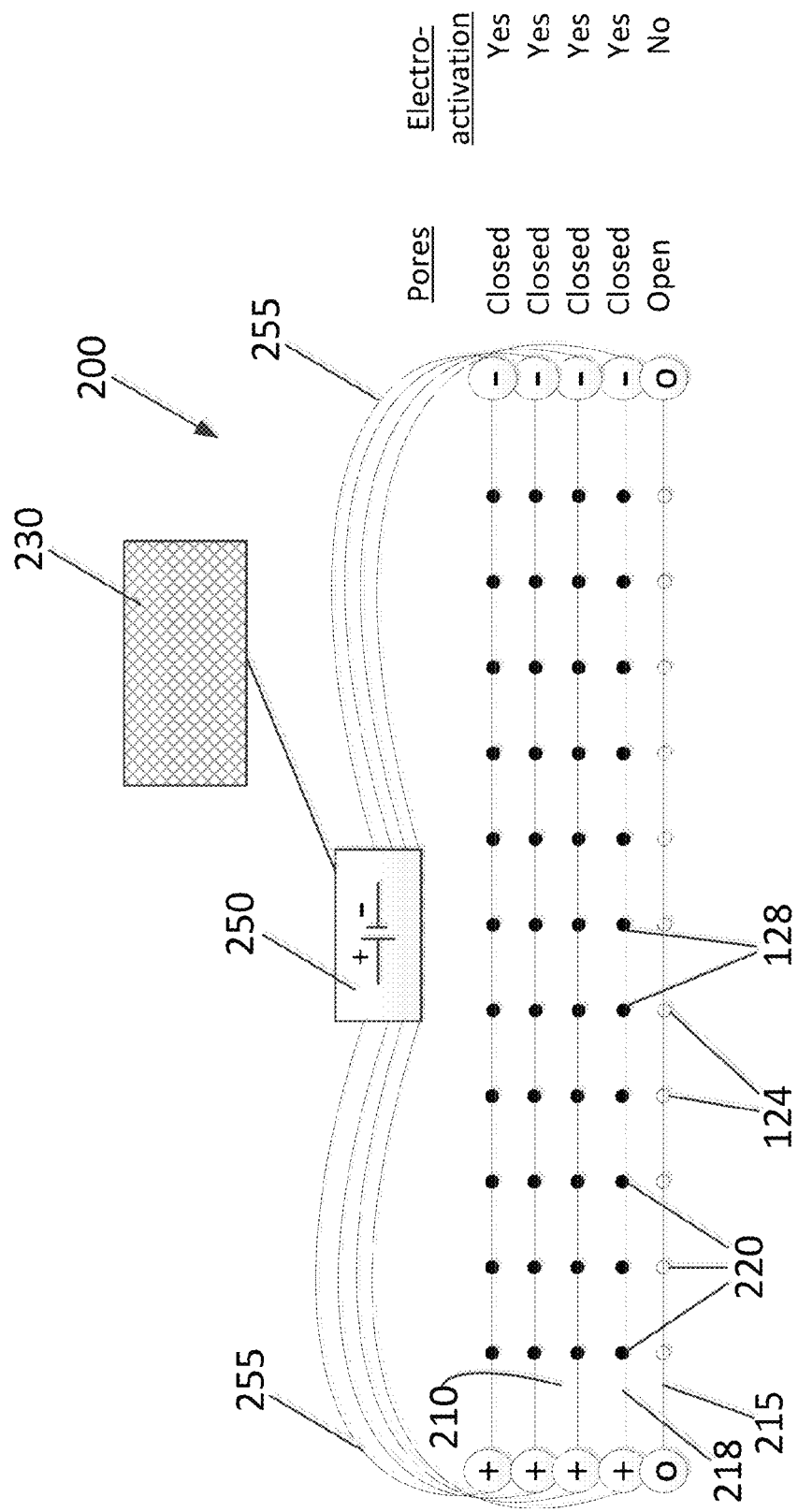
FIG. 2 depicts a diagrammatic view of an aspect of a device.

FIG. 2 depicts a diagrammatic view of an aspect of a device 200 comprising: a multilayer membrane 210 including a plurality of layers 218, each layer of the plurality of layers having a plurality of variably-sized pores 220; an electroactive polymer 224, 228 within the each layer 218 and surrounding each of the plurality of variably-sized pores 220; and a controller 230 operably connected to sequentially activate the electroactive polymer to alter one or more sizes of the plurality of the variably-sized pores 220 within a first layer 215 of the multilayer membrane and to sequentially alter one or more sizes of the variably-sized pores 220 sequentially within a second layer 218 and one or more subsequent layers 218 of the multilayer membrane 210; wherein at least one of the plurality of the variably-sized pores 220 in the first layer is aligned with at least one of the plurality of variably-sized pores in one or more subsequent layers 210 of the multilayer membrane.

The device 200 includes the controller 230 and circuitry including a battery 250 is used to draw an electrical potential across each membrane layer 210. Electronic activation 255 of the membranes controls the passage of fluid through the multilayer membrane 210. For example, multilayer membranes 210 comprised of electroactive polymers 224, 228 can act as valves with pores approximately 0.1-5.0 µm in diameter that open 224 or close 228 depending on the oxidation state of the polymers.

FIGS. 3A, 3B, and 3C depict a diagrammatic view of an aspect of a device 300 comprising: a multilayer membrane 310 including a plurality of layers, each layer of the plurality of layers having a plurality of variably-sized pores 320; an electroactive polymer 324, 328 within the each layer 315, 318 and surrounding each of the plurality of variably-sized pores 320; and a controller 330 operably connected to sequentially activate the electroactive polymer 324, 328 to alter one or more sizes of the plurality of the variably-sized pores within a first layer 315 of the multilayer membrane and to sequentially alter one or more sizes of the variably-sized pores 320 sequentially within a second layer 318 and one or more subsequent layers of the multilayer membrane 310, wherein at least one of the plurality of the variably-sized pores 320 in the first layer 315 is aligned with at least one of the plurality of variably-sized pores 320 in one or more subsequent layers 318 of the multilayer membrane 310.

The device 300 includes the controller 330 and circuitry including a battery 350 is used to draw an electrical potential across each membrane layer 310. Electronic activation 355 of the membranes controls the passage of fluid through the multilayer membrane 310. For example, multilayer membranes 310 comprised of electroactive polymers 324, 328 can act as valves with pores approximately 0.1-5.0 µm in diameter that open 324 or close 328 depending on the oxidation state of the polymers.

The controller 330 controls a battery 350 to delivery an electrical potential 355 of the electroactive polymers 324, 328 in the plurality of membranes 310 so that pores within the membranes are in an open 324 or closed 328 state within each layer of the multilayer membrane. In step 1 (FIG. 3A), a first layer 313 of the multilayer membrane is comprised of electroactive polymers that are in an open state 324. The second 315 and third layers 318 of the multilayer membrane 310 are comprised of electroactive polymers that are in a closed state 328.

In step 2 (FIG. 3B), a second 315 layer of the multilayer membrane is comprised of electroactive polymers that are in an open state 324. The first 313 and third 318 layers of the multilayer membrane 310 are comprised of electroactive polymers that are in a closed state 328.

In step 3 (FIG. 3C), a third 318 layer of the multilayer membrane is comprised of electroactive polymers that are in an open state 324. The first 313 and second 315 layers of the multilayer membrane 310 are comprised of electroactive polymers that are in a closed state 328. The sequential opening 324 and closing 328 of pores in each layer of the multilayer membrane 310 in steps 1, 2, and 3 may act to draw fluid out of a wound of the mammalian subject. The sequential opening and closing of pores draw fluid through each layer of the multilayer membrane 310. A peristaltic pump may be used to enhance fluid flow out of the multilayer membrane 310 and into a fluid collection reservoir. Active pumping from each membrane compartment 310 is coordinated by the controller 330 to coincide with opening 324 and closing 328 of the membrane pores as described above.

FIG. 4 depicts a diagrammatic view of an aspect of a device 400 including a multilayer membrane 410 comprising a plurality of pores 420 of variable size is used to control the flow 430 of cerebral spinal fluid (CSF) in a patient with hydrocephalus. A cerebral shunt composed of a ventricular catheter 480, a distal catheter 490 and a membrane device 400 with a pressure sensor 440 is implanted to control intracranial pressure in the patient. The flow 430 of CSF fluid from the lateral ventricle 480 of the brain to the peritoneal cavity is controlled by a controller 450 in the multilayer membrane device which monitors intracranial pressure and responsively adjusts the fluid flow rate.

A device 400 includes a multilayer membrane 410 including a plurality of layers 410, each layer of the plurality of layers having a plurality of pores 420 on the plurality of layers of the multilayer membrane; an actuator 460, 470 operably attached to the plurality of layers 410 of the multilayer membrane; and a controller 450 operably activating the actuator 460, 470 to alter a relative lateral position of two or more layers 410 of the plurality of layers to align two or more of the plurality of pores 420 within the two or more layers 410 of the plurality of layers of the multilayer membrane; wherein the two or more pores 420 are aligned and accessible through the two or more layers 410 of the plurality of layers of the multilayer membrane.

Figures 5A, 5B, 5C:
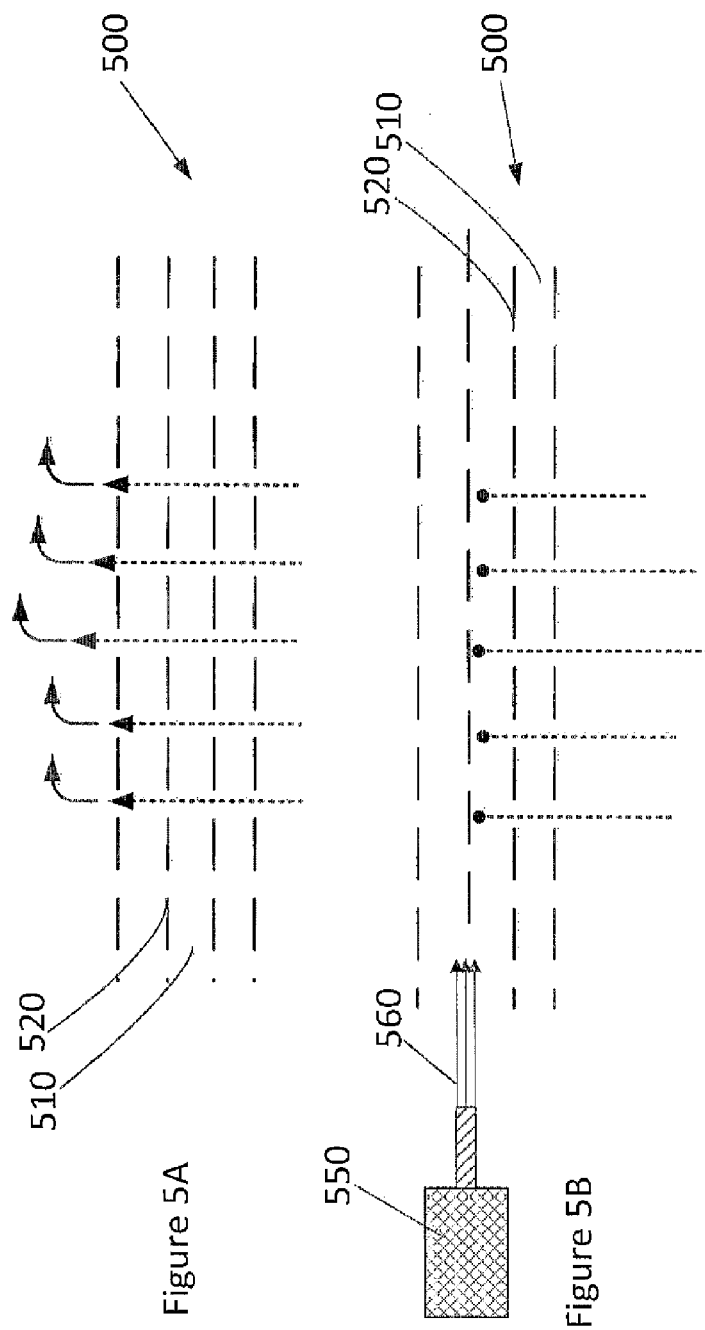
FIGS. 5A, 5B, and 5C depict a diagrammatic view of an aspect of a device.

FIGS. 5A, 5B, and 5C depict a diagrammatic view of an aspect of a device 500 including a multilayer membrane 510 including a plurality of layers 510, each layer of the plurality of layers having a plurality of pores 520 on the plurality of layers of the multilayer membrane; an actuator 560 operably attached to the plurality of layers 510 of the multilayer membrane; and a controller 550 operably activating the actuator 560 to alter a relative lateral position of two or more layers 510 of the plurality of layers to align two or more of the plurality of pores 520 within the two or more layers 510 of the plurality of layers of the multilayer membrane; wherein the two or more pores 520 are aligned and accessible through the two or more layers 510 of the plurality of layers of the multilayer membrane; a multilayer membrane 510 comprising a plurality of pores 520 of variable size; a controller 550 responsive to a conditional stimulus configured to alter a relative position 560 of two or more layers of the multilayer membrane 410 to align 560 one or more identical sizes 520 of the pores within a plurality of layers of the multilayer membrane; wherein the one or more identical sizes 520 of the pores are aligned and accessible through the plurality layers of the multilayer membrane in response to the conditional stimulus.

FIG. 5A depicts a diagrammatic view of an aspect of a device 500 comprising: a multilayer membrane 510 comprising a plurality of pores 520 of variable size, e.g., 5.0 µm. A controller 550 responsive to a conditional stimulus configured to activate an actuator 560 to alter a relative position of two or more layers of the multilayer membrane 510 to align by the actuator 560 one or more identical sizes 520 of the 5.0 µm pores to allow flow through a plurality of layers of the multilayer membrane. The one or more 5.0 µm sizes 520 of the pores are aligned and accessible through the plurality layers of the multilayer membrane in response to the conditional stimulus.

FIG. 5B depicts a diagrammatic view of an aspect of a device 500 comprising: a multilayer membrane 510 comprising a plurality of pores 520 of variable size, e.g., 5.0 µm. A controller 550 responsive to a conditional stimulus is configured to actuate an actuator 560 to alter a relative position of two or more layers of the multilayer membrane 510 and to alter alignment 560 of one or more identical sizes 520 of the 5.0 µm pores in order to block flow through a plurality of layers of the multilayer membrane. The one or more 5.0 µm sizes 520 of the pores are not aligned and flow through the plurality layers of the multilayer membrane is not accessible in response to the conditional stimulus.

FIG. 5C depicts a diagrammatic view of an aspect of a device 500 comprising: a multilayer membrane 510 comprising a plurality of pores 520 of variable size, e.g., 5.0 µm or 0.1 µm. A controller 550 responsive to a conditional stimulus is configured to activate an actuator 560 to alter a relative position of two or more layers of the multilayer membrane 510 and to align 560 one or more identical sizes 520 of the 5.0 µm pores to allow flow through a plurality of layers of the multilayer membrane and to block flow through 0.1 µm pores of the multilayer membrane. The one or more 5.0 µm sizes 520 of the pores are aligned and accessible through the plurality layers of the multilayer membrane in response to the conditional stimulus.

FIGS. 6A, 6B, 6C, 6D, and 6E depict a diagrammatic view of an aspect of a device 600 comprising: a multilayer membrane including a plurality of layers 610, each layer of the plurality of layers 610 having a plurality of variably-sized pores 620; an electroactive polymer 624, 628 within the each layer 615, 618 and surrounding each of the plurality of variably-sized pores 620; and a controller 630 operably connected to sequentially activate the electroactive polymer 624, 628 to alter one or more sizes of the plurality of the variably-sized pores within a first layer 615 of the multilayer membrane and to sequentially alter one or more sizes of the variably-sized pores 620 sequentially within a second layer 618 and one or more subsequent layers of the multilayer membrane 610, wherein at least one of the plurality of the variably-sized pores 620 in the first layer 615 is aligned with at least one of the plurality of variably-sized pores 620 in one or more subsequent layers 618 of the multilayer membrane.

The at least one of the plurality of the variably-sized pores 620 in the first layer 615 aligned with the at least one of the plurality of variably-sized pores in one or more subsequent layers 618 of the multilayer membrane are accessible to fluid flow 640 through a plurality of layers 610 of the multilayer membrane in response to the conditional stimulus.

In FIGS. 6A, 6B, 6C, 6D, and 6E, the controller 630 is operably connected to activate the electroactive polymer 624, 628 in the plurality of layers 610 of the multilayer membrane to produce peristaltic pumping activity (FIG. 6A through FIG. 6E) by aligned variably-sized pores 620 in three or more layers 615, 618 of the multilayer membrane 610. The peristaltic pumping activity of the multilayer membrane 610 produces sequential fluid flow 640 through the variably-sized pores 620 surrounded by the electroactive polymer 624, 628 in the three or more layers 618 of the multilayer membrane 610.

Figure 7:
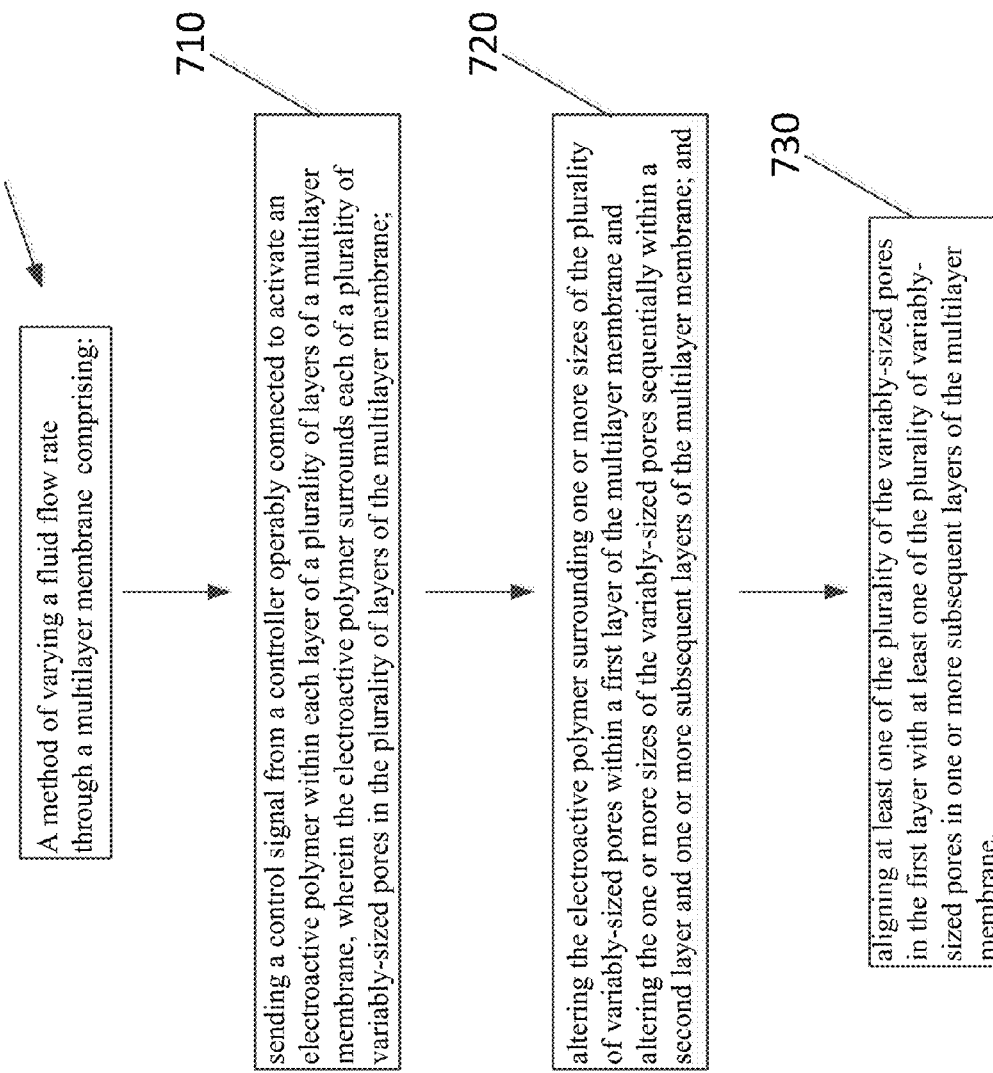
FIG. 7 depicts a diagrammatic view of an aspect of a method.

FIG. 7 depicts a diagrammatic view of an aspect of a method. A method 700 of varying a fluid flow rate through a multilayer membrane includes: sending 710 a control signal from a controller operably connected to activate an electroactive polymer within each layer of a plurality of layers of a multilayer membrane, wherein the electroactive polymer surrounds each of a plurality of variably-sized pores in the plurality of layers of the multilayer membrane; altering 720 the electroactive polymer surrounding one or more sizes of the plurality of variably-sized pores within a first layer of the multilayer membrane and altering the one or more sizes of the variably-sized pores sequentially within a second layer and one or more subsequent layers of the multilayer membrane; and aligning 730 at least one of the plurality of the variably-sized pores in the first layer with at least one of the plurality of variably-sized pores in one or more subsequent layers of the multilayer membrane.

Figure 8:
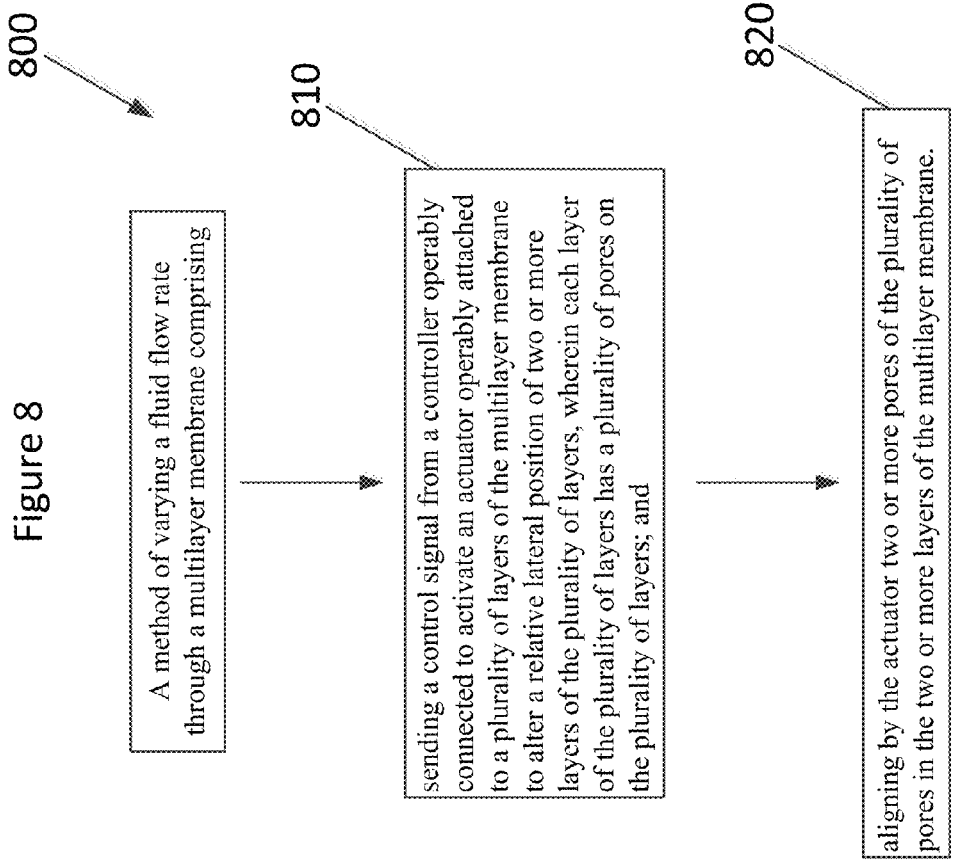
FIG. 8 depicts a diagrammatic view of an aspect of a method.

FIG. 8 depicts a diagrammatic view of an aspect of a method. A method 800 of varying a fluid flow rate through a multilayer membrane includes: sending 810 a control signal from a controller operably connected to activate an actuator operably attached to a plurality of layers of the multilayer membrane to alter a relative lateral position of two or more layers of the plurality of layers, wherein each layer of the plurality of layers has a plurality of pores on the plurality of layers; and aligning 820 by the actuator two or more pores of the plurality of pores in the two or more layers of the multilayer membrane.

The device may include an ultraviolet (UV) illumination source to provide self-sterilization of the device. A controller may send a control signal to a UV illumination source to activate self-sterilization of the device. The controller may include operational programs for self-cleaning the device. Self-cleaning of the device may occur by washing the membranes with an aqueous solution such as normal saline at prescribed intervals to ensure that the pores maintain a clear flow. If the device is located on or within the subject's body, additional fluids could be absorbed by the subject's body via natural means.

A device includes a multilayer membrane having a plurality of layers, each layer of the plurality of layers having a plurality of variably-sized pores. The plurality of layers may be constructed of an electroactive polymer to form the variably sized pores. Alternatively, the pores may be formed from short DNA subunits to form the pores. Computer design will fit the DNA subunits together to form the pores. The pores constructed from DNA subunits may be of dimensions 14 nm in length and 5.5 nm in diameter. This formed the main part of their artificial nanopore.

To overcome hydrophilicity of the DNA subunits to embed in a hydrophobic membrane, the scientists chemically attached to the DNA subunits to Porphyrin molecules that will anchor the DNA subunits within a lipid membrane. These structures were then able to embed the DNA subunit tubes within the membrane. See, e.g., Burns et al., *Angewandte Chemie International Edition*, Volume 52, Issue 46, page 11943, Nov. 11, 2013, which is incorporated herein by reference. A device may include a multilayer membrane having a plurality of layers, each layer of the plurality of layers having a plurality of variably-sized pores may be used to detect the presence of bacteria or other contaminants in situ with the device. For example, the device may detect red blood cells (6-8 μm) in the urine; bacteria (0.2 to 30 μm) in a wound; yeast (0.3 to 8 μm), viruses (0.005 to 0.1+μm), poliovirus (2.37 μm). The in situ data from analysis of cells passing through the multilayer membrane dependent upon pore size is useful diagnostic data during on-going treatment. See, e.g., "Relative Pore Size Chart for filtration", Spectrumlabs.com, which is incorporated herein by reference.

Fabrication of a Multilayer Membrane Comprising a Plurality of Variably-Sized Pores The device includes a multilayer membrane including each layer of the multilayer membrane comprising a plurality of variably-sized pores. The multilayer membrane may be made a wide range of conducting polymer membranes to suit particular target applications. These include free standing membrane based on both polypyrrole and polyaniline with a variety of counterions, composite films, and co-polymers. The counterions used have varied from simple ones such as pTS to large polyelectrolytes such as heparin. Examples of the types of membrane that have been produced may depend upon the conductivity and tensile strength desired in the membrane. Examples of the composition of the membrane include, but are not limited to, polypyrrole-benzenesulfonate; polypyrrole-1,3-benzenedisulfonate; polypyrrole-dodecylsulfate; polypyrrole-4-ethylbenzene sulfonate; polypyrrole-2-mesity lenesulfonate; polypyrrole-1,5-naphthalene disulfonate; polypyrrole-paratoluenesulfonate; polypyrrole-paratoluenesulfonate/dodecylsulfate; polypyrrole-poly(vinylsulfonate) composite; polypyrrole-nafion composite; poly(3-carboxy-4-methylpyrrole)-paratoluenesulfonate; copolymer of pyrrole with 3-carboxy-4-methylpyrrole; poly aniline.

In addition, to the free standing and composite membranes, techniques may be developed for fabricating thin CEP films onto conventional substrates. A thin selective layer is formed with superior flux characteristics. Conventional substrates such as polysulfone (PS) or poly vinylidene fluoride (PVDF) are sputtered with a thin film of platinum. The platinum layer does not unduly block the pores of the substrate and does not affect the bulk permeability. The platinised substrate is then used as a working electrode and a thin layer of conducting polymer is electrochemically deposited. The film acts as a selective barrier for transport.

Two different types of application of the coated platinised films may be considered. In the first example, the redox properties of the CEP film may be used to induce transport. In the second one, a membrane may have a platinum coating on both sides. In this example the polymer acts as a thin selective layer.

Separation of Mineral Ions.

Polypyrrole-pTS may be electrochemically deposited onto a PVDF substrate by a galvanostatic method (2 mA cm$^{-2}$) and grown for 3 minutes from a solution containing 0.2 M pyrrole monomer and 0.05 M pTS to give a coating of about 4 μm. The coated membrane was then used to separate copper (II) ions from iron (III) in solution. The transport may be carried out with a feed solution containing 0.1 M Copper (II) and 0.1 M iron (III) in 0.01 M H2S04. The receiving solution contains 0.01 M H2S04. The electrical pulse potential used may be −0.4V-+0.6V with a pulse width of 20 seconds.

When an electrical pulse potential is applied, copper is preferentially transported across the membrane, with a separation factor of 5. In this example, the application of potential to the film may induce not only redox changes in the polymer but also reduced copper(II) to copper metal onto the surface of the polymer and subsequently re-oxidized it. Because of the kinetics the copper(II) are thus pre-concentrated in the vicinity of the polymer-solution interface and are insert into the reduced polypyrrole. Another point of interest is that the transport of copper (U) continues for a long time after the applied potential is switched off. During application of potential, the membrane becomes loaded with copper metal. This metal slowly reoxidises after the potential waveform is stopped.

Transport of Proteins.

Conducting polymer coated platinised substrates may also be used to separate proteins. The PVDF substrate is platinised on both sides and coated with Ppy/pTS on one side. Instead of applying a squarewave potential in a three electrode system, there is now a two electrode system, namely the two sides of the membrane. The separation of the electrodes is thus controlled and small, only 110 μm. If a constant current is applied between the electrodes, the system acts as an electrophoretic system with a high electric field. The results of a test separation experiment of human serum albumin (HSA) and myoglobin, two proteins of similar molecular weight using a double-sided platinum coated PVDF membrane, has been shown. The feed solution was a mixture of HSA (670 ppm or 10 μM) and Myoglobin (175 ppm or 10 μM) in Milli-Q water whilst the permeate solution was Milli-Q water. A current density of 1.28 mA cm$^{-2}$ is applied with the cathode facing the feed solution. PPy/pTS was deposited on one side of the Pt/PVDF at 1 mA cm$^{-2}$ for 60 s. Significant HSA transport occurs across the film.

Nearly one third of the HAS may be transferred in six hours. No myoglobin is detected (<0.2 ppm) in the permeate side. This very effective separation is due partly to the pI of the two proteins. At pH 6.5 HSA (pI=4.8) is negatively charged whilst Myoglobin (pI=7.5) has a positive charge. The CEP coating allows different selectivities by incorporating particular selective functional groups into the polymer and changing the hydrophobicity of the surface layer. In this case the polymer layer effectively eliminates the Myoglobin transport, increasing the selectivity markedly (by a factor of over 6). See, e.g., W. E. Price et al. *Synthetic Metals* 102: 1338-1341, 1999, which is incorporated herein by reference.

Etching Process Using Ion-Beam Technology

The device including a multilayer membrane includes pores that may be created with an etching process using ion-beam technology. For nitrate treatment, the membrane pores are about 10 nanometers in diameter. Membrane samples may contain about 1 billion holes per square centimeter. See, e.g., U.S. Pat. No. 7,632,406, which is incorporated herein by reference.

Electrically-Driven Fluidic Valve Comprising a Microporous Membrane

The device including a multilayer membrane includes a plurality of variably-sized pores. One or more types of electroactive polymer surround the plurality of variably-sized pores. The electroactive polymer may be a conjugated polymer including, but not limited to, polyaniline, polypyrrole, polythiophene, polyp araphenylvinylene, poly(p-pyridylvinylene) and derivatives thereof.

The multilayer membrane may be a microporous membrane having pores varying in size between 0.1 and 5 μm.

To cover the multilayer membrane as the microporous membrane with an electroactive polymer, it is necessary to make the membrane conductive. The microporous membrane may be rendered conductive by a metalization process.

The device includes a multilayer membrane may include each layer of the multilayer membrane comprising a plurality of variably-sized pores. The operation of the multilayer membrane as a microporous membrane including the variably-sized pores is based upon changing the oxidation-reduction state of the electroactive polymer covering the pores of the membrane. When the variably-sized pores are closed, that is to say when the polymer covers the pores of the membrane, the polymer is in the oxidized state. In this state, the anion of the electrolytic salt is inserted into the polymer, resulting in an increase in the diameter of the polymeric fibers.

The multilayer membrane including variably-sized pores is opened by changing the oxidation-reduction state of the polymer, namely by changing it from the oxidized state to the reduced state. To change the oxidation-reduction state of the polymer, the multilayer membrane is exposed in the presence of an electrolytic solution containing a solvent, such as acetonitrile, and an electrolyte salt is used to functionalize the microporous membrane, but in the absence of monomers. This electrolyte salt is identical to the one used in the method of functionalizing the variably-sized pores by polymerization. However, in alternative aspects, it is possible to use other electrolytic solutions such as an aqueous solution of NaCl. The electrolytic salt is contained in the solution with a concentration lying in the range from $10^{-1}$ to $5 \times 10^{-1}$ mol/l.

To change the oxidation-reduction state of the electroactive polymer that form variably-sized pores in the multilayer microporous membrane, a voltage may be applied to the terminals of the cell holding the multilayer membrane. This voltage varies on either side of the oxidation-reduction potential of the polymer used. Preferably, the voltage applied varies between −5 and +5 volts, depending on whether it is desired to oxidize or reduce the polymer.

The variably-sized pores of the multilayer membrane may have an opening and closing time lying between 1 and 100 milliseconds, depending on the pore diameter of the microporous multilayer membrane, which may vary between 0.2 and 1 μm. See, e.g., U.S. 2006/0138371, which is incorporated herein by reference.

Device Including a Self-Priming Pump

The device includes a multilayer membrane wherein each layer of the multilayer membrane comprises a plurality of variably-sized pores that may utilize a self-priming peristaltic pump actuated with a single linear actuator. The pump is tolerant of bubbles and particles and can pump liquids, foams, and gases. The pump may be actuated by a motor and/or a shape memory alloy (SMA) wire; or may be manually actuated. The pump may include a Delrin acetal plastic body with two integrated valves, a flexible silicone tube, and an actuator. Pumping is achieved as the forward motion of the actuator first closes the upstream valve, and then compresses a section of the tube. The increased internal pressure opens a downstream burst valve to expel the fluid. Reduced pressure in the pump tube allows the downstream valve to close, and removal of actuator force allows the upstream valve and pump tube to open, refilling the pump. The motor actuated design offers a linear dependence of flow rate on voltage in the range of 1.75-3 V. Flow rate may decrease from a value of 780 μl/min (with an increase in back pressure) to a maximum back pressure of 48 kPa. At 3V and minimum back pressure, the pump consumes 90 mW. The shape memory alloy actuated design offers a 5-fold size and 4-fold weight reduction over the motor design, higher maximum back pressure, and substantial insensitivity of flow rate to back pressure at the cost of lower power efficiency and flow rate. The manually actuated version is simpler and appropriate for applications unconstrained by actuation distance.

The device includes a multilayer membrane wherein each layer of the multilayer membrane comprises a plurality of variably-sized pores that may utilize miniature fluid pumps. For many applications, a miniature pump would supply sufficient flow rate and pressure, while having a low voltage requirement, low power consumption, a simple control system, and low cost. Peristaltic pumps move fluid by exerting forces on the outside of a pumping chamber, which often consists of a flexible tube containing the fluid. Many peristaltic pumps have the advantage that the pump actuator components do not touch the fluid and that the pumping chamber can be made disposable to ensure sterility and prevent cross-contamination. Miniature peristaltic pumps have been microfabricated using polydimethylsiloxane (PDMS), PDMS bonded to glass, or glass bonded to silicon. In most of these, a series of two or more actuators compress regions of a channel (the pumping chamber) to produce a peristaltic wave. In other miniature peristaltic designs, the pump chamber is created from a section of flexible tubing and the pumping action is created by motor-driven rollers, magnetic balls, or drops of magnetic liquid which compress the tube.

A miniature peristaltic pump may use a single reciprocating actuator motion to produce pumping. This pump may use off-the-shelf tubing and may be manufactured using conventional materials and methods including injection molding, stereolithography, or CNC machining. The pump consumes 90 mW of electrical power at 3V, and allows control of flow rate by controlling voltage. Although here we present only one size of the pump, we have created smaller and larger versions which achieve 0.1× to 5× the nominal flow rate and/or higher back pressures (up to 69 kPa).

In some aspects, the pump may be driven by a gear motor shown in various phases of the pumping cycle. The pumping chamber and inlet and outlet connections are a single piece of commercially available silicone tubing. In some aspects, the pump with motor is 8 mm×22 mm×35 mm, weighs 3.6 g, and consists of four parts: motor, cam, pump body, and tube. The pumping cycle may be described in three phases. Phase 1: Cam rotation pushes down on the plunger arm, pinching the tubing and creating the upstream valve. Phase 2: Further motion of the plunger arm rotates the plunger clockwise (about the protrusion of the upstream valve), compressing the pumping chamber. Increased pressure in the pumping chamber causes the downstream burst valve to open, expelling fluid from the pumping chamber. Phase 3:

The downstream valve closes as pressure is reduced in the pumping chamber. As the cam rotates further, it allows the plunger arm to spring upward, and the elasticity of the tubing and line pressure open the upstream valve. The pumping chamber draws liquid through the now-open upstream valve into the pumping chamber.

A miniature peristaltic pump design may use a single (linear) actuator motion to effect both valving and pumping actions. A pump may utilize a motor, SMA, and/or manually actuated versions of the design. The pump is self-priming, tolerant of bubbles and particles, can pump liquids, foams, and gases, and can be manufactured using conventional materials and methods such as injection molding or CNC machining. All designs may be fabricated from Delrin acetal plastic and a flexible silicone tube acts as the pump chamber.

The motor actuated pump's flow rate is linearly dependent on driving voltage in the range of 1.75-3V against a constant back pressure, allowing for easy regulation of flow rate. Pump flow rate decreases from 780 µl/min to the maximum back pressure of 48 kPa. The pump consumes ~90 mW of power when pumping against minimal back pressure at 3V. However, we estimate only 6% of this power is used to drive the liquid while over 60% of the power is consumed by the motor and gearbox, motivating improvement in the choice of the actuator. This pump system measures 8 mm×22 mm×35 mm and weighs 3.6 g.

The SMA actuated pump offers lower flow rates (a maximum of 60l/min) and lower flow rate per power (0.14 µl min$^{-1}$ mW$^{-1}$). However, it offers a 5-fold package volume reduction and 4-fold weight reduction over the motor actuated pump, and allows for further downscaling. The manually actuated design is simpler and intended for situations where travel distance of actuator is not a design constraint. See, e.g., V. Shkolnikov et al., *Sensors and Actuators A* 160: 141-146, 2010, which is incorporated herein by reference.

Device Including a Peristaltic Polydimethylsiloxane (PDMS) Micropump

The device utilizing a peristaltic PDMS micropump may be actuated by the thermopneumatic force. The peristaltic PDMS micropump includes the three peristaltic-type actuator chambers with microheaters on the glass substrate and a microchannel connecting the chambers and the inlet/outlet port. The micropump may be fabricated by the spin-coating process, the two-step curing process, the molding process using negative photoresist. The diameter and the thickness of the actuator diaphragm are 2.5 mm and 30 m, respectively. The maximum flow rate of the micropump is about 0.36 L/s at 2 Hz for the zero hydraulic pressure difference, when the three-phase input voltage is 20V.

A PDMS micropump with a mechanical actuator fabricated by using multi-stacked PDMS-molding technique may be utilized with the device including a multilayer membrane wherein each layer of the multilayer membrane comprises a plurality of variably-sized pores. The membrane-type micropumps with various actuators have advantages and disadvantages from the viewpoint of power consumption, integration method, response time, operation frequency and voltage, fabrication process, and actuation efficiency. For the simple fabrication process and the large volume stroke of the micropump, the thermopneumatic actuation method may be used.

The micropump requires a microvalve unit for the one-way flow rate of the working fluid. Microvalves are classified into the passive and active valves. The active valve is useful to control the flow rate under the some pressure difference, but its fabrication process is complicated. The passive check valve opens only to the forward pressure and have simple structures compared to the active valve. However, with the passive check valve, the control of reverse flow rate under the pressure difference is impossible.

In alternative aspects, the peristaltic micropump using the thermopneumatic actuation may be used. The peristaltic-type actuators can be operated as the dynamic valves and controlled easily by the applied electric input power without any additional process for the fabrication of the microvalves unit.

See, e.g., O. C. Jeong et al., *Sensors and Actuators A* 123-124: 453-458, 2005, which is incorporated herein by reference.

Method of Operation of Sensors for Detection of Moisture

A moisture sensor may be attached to the device including a multilayer membrane to serve as a wound dressing or bandage on a wound. Before applying the dressing the clinician may cleanse the wound as per best practice guidelines and place the device including a multilayer membrane and the sensor onto the wound, ensuring that a porous, non-adhesive coating of the sensor is placed downwards. The porous non-adhesive cover is bonded to the sensor pair but can be cut to a smaller size if the device and dressing chosen for use with the sensor is smaller than the area of the non-adhesive cover. Sensor tags, found at the end of the paired sensor electrodes, are taped down at the edge of the dressing (if an adhesive dressing is used). The longer sensor, as used in this study for leg ulcers, can have the tags tucked into the patient's bandage.

The device including a multilayer membrane and a moisture sensor may be attached to a wound dressing or bandage on a wound. To read the moisture level, the tags on the moisture sensor are freed from the edge of the dressing or bandage and the portable meter is clipped onto them. The meter applies a low, alternating current to the sensor. The sensor is made up of a pair of small, silver chloride electrodes. The low current applied through the paired sensor electrodes does not interfere with local tissue or patient comfort and after ten to thirty seconds a reading of moisture level is obtained, based on the value of electrical impedance across the sensor electrodes. As ions and other charged molecules move in the wound exudate under the influence of electric current, it is possible to relate electrical impedance readings to five useful clinical bands of moisture level at the wound interface. Dry environments do not allow charges to move around and cause high electrical impedance readings, wet environments lead to easy charge movement and low impedance readings. The desired "moist" condition is a range of impedance located between the high and low values.

The five moisture bands discernable from the sensor readings are:

Dry: electrically high impedance

Dry to moist: impedance falling from high levels to mid-range

Moist: mid-range impedance

Moist to wet: impedance tending to low

Wet: low impedance.

The device may include a controller in communication with the moisture sensor to determine the moisture band reading and to use that reading to signal the device to adjust pumping action of the device. For example, a "wet" reading should trigger increased moisture removal by the device, A "moist to wet" reading might not trigger activation of the device and result in reduced pumping activity by the device. See, e.g., McColl et al., *Wounds UK*, 5: 94-99, 2009, which is incorporated herein by reference.

Device for Wound Treatment, Wound Healing, and Exudate Management

The device may measure the rate of exudate fluid accumulation in a reservoir attached to the device. The moisture levels in the wound are recorded by the controller and analyzed by the control circuitry to use that reading to signal the device to adjust pumping action of the device. Methods may be utilized to evaluate wound healing based on exudate fluids and wound moisture level. Wound exudate must be effectively managed if the optimal moist environment necessary for wound healing is to be created, and the surrounding skin protected from the risks of maceration. The production of wound exudate occurs as a result of vasodilation during the early inflammatory stage of healing under the influence of inflammatory mediators such as histamine and bradykinin. It presents as serous fluid in the wound bed and is part of normal wound healing in acute wounds. However, when the wound becomes chronic and non-healing with persistent, abnormal inflammation or when infection becomes established, exudate takes on a different guise and generates clinical challenges. In the chronic wound, exudate contains proteolytic enzymes and other components not seen in acute wounds. This type of exudate has justifiably been termed a wounding agent in its own right because it has the capacity to degrade growth factors and pal-wound skin and predispose to inflammation. In order to develop an effective management approach, the clinician must be able to accurately assess and understand the implications of the composition and quantity of exudate present in the wound.

Exudate Composition.

Wound exudate is derived from serum through the inflammatory/extravasation process. Acute wound exudate contains molecules and cells that are vital to support the healing process. It has a high protein content (although lower than that found in serum), with a specific gravity greater than 1.020. Its composition includes electrolytes, glucose, cytokines, leukocytes, metalloproteinases, macrophages and micro-organisms. In the first 48 to 72 hours after wounding, platelets and fibrin may be present, but this reduces as bleeding diminishes.

TABLE 1

Some constituents of exudate and their functions.
Component/Function

Fibrin/Clotting.
Platelets/Clotting.
Polymorphonuclearcytes (PMNs)/Immune defense, production of growth factors.
Lymphocytes/Immune defense.
Macrophages/Immune defense, production of growth factors.
Micro-organisms/Exogenous factor.
Plasma proteins, albumin, globulin, fibrinogen/Maintain osmotic pressure, immunity, transport of macromolecules.
Lactic acid/Product of cellular metabolism and indicates biochemical hypoxia.
Glucose Cellular energy source.
Inorganic salts/Buffering, pH hydrogen ion concentration in a solution.
Growth factors/Proteins controlling factor-specific healing activities.
Wound debris/dead cells No function.
Proteolytic enzymes/Enzymes that degrade protein, including serine, cysteine, aspartic proteases and matrix metalloproteinases (MMPs)
Tissue inhibitors of metalloproteinases (TIMPS)/Controlled inhibition of metalloproteinases.

As fluid passes through the inflamed vessel walls (extravasation), the wound exudate consists of modified serum and will therefore contain similar solutes. As it arrives at the wound surface, this fluid may be contaminated with tissue debris and microorganisms. Healing acute wounds produce exudate containing active growth factors. These are not present in chronic wounds.

See, e.g., White and Cutting, *Modern exudate management: a review of wound treatments*, 2006, which is incorporated herein by reference.

Device Including Electrostrictive Actuators to Control Pore Diameter within the Multilayer Membrane The device may include a supporting frame that supports the multilayer membrane. A supporting base may be connected to a strut assembly. The strut assembly may be connected to additional structure within the overall structural system. The supporting base/strut assembly structure is indicative of usual support and overall system interface for membrane structures. A controller may activate actuators affixed to supporting base adjacent to the supporting base periphery to initiate fluid flow through the multilayer membrane. Upon initiation of fluid flow, actuators bend upon electrical activation. Electrostrictive actuators may be used having high mechanical modulus and strain combination. In some embodiments an actuator may be incorporated into a polymer-polymer actuator bed. See, e.g., U.S. Pat. No. 6,724,130; U.S. Pat. No. 6,545,391; and U.S. Pat. No. 7,015,624, which are incorporated herein by reference.

Device Having a Multilayer Membrane and Including a Pressure Sensor

The device including a multilayer membrane may include a pressure sensor to monitor intracranial pressure, e.g., resulting from flow of cerebral spinal fluid, wherein the pressure sensor may signal to control circuitry on the device. For example, a passive resonant sensor may be used to monitor intracranial pressure and to wirelessly signal to control circuitry. A wireless, real-time pressure monitoring system with passive, flexible; millimeter-scale sensors may be scaled down to dimensions of 1×1×0.1 cubic millimeters. This level of dimensional scaling is enabled by sensor design and detection schemes, which overcome the operating frequency limits of traditional strategies and exhibit insensitivity to lossy tissue environments. The system may be used to capture human pulse waveforms wirelessly in real time as well as to monitor in vivo intracranial pressure continuously using sensors down to 2.5>2.5×0.1 cubic millimeters. Printable wireless sensor arrays may be used in real-time spatial pressure mapping.

Passive Resonant Sensors.

A pressure-sensitive capacitive element sensor may be integrated with an inductive antenna to form a resonant circuit, which has a unique resonant frequency under zero pressure. To achieve size scalability, a distributed resonant tank may be created by stacking a deformable dielectric layer between the two inductive spirals in a sandwich structure. Under applied pressure, the separation distance between the spiral layers is reduced, increasing the effective coupling capacitance and shifting the resonant frequency down to lower frequencies. The spiral layers are printed or lithographically patterned on flexible polyimide substrates, while the pressure sensitive dielectric layer is implemented with a microstructured styrene-butadiene-styrene (SBS) elastomer. The microstructured elastomer dielectric sensor has been shown to be more sensitive than its unstructured counterpart. The improved sensitivity is due to reduced viscoelastic behavior of thin films and the change in effective permittivity of the region between the plates under compression, in addition to the change in separation distance. The pyramidal elastomer microstructures deform to fill in the air gaps between them with applied pressure, thus increasing the effective permittivity. This sandwich form enables a simple low-cost method of wax printing process by eliminating the need for vias to connect discrete inductive and capacitive structures in parallel. SBS elastomer may be used instead of other commonly known elastomers, such as poly(dimethyl siloxane) (PDMS) or polyurethane, due its low loss in the high frequency range. However, one drawback when using SBS is the drift in capacitance values during cycling measurements.

Wireless real-time monitoring may be demonstrated in the device having a multilayer membrane with a system of passive, flexible millimeter-scale sensors as small as 1×1× 0.1 mm$^3$. The sensor devices are more than an order of magnitude smaller in volume than recent research devices for pressure sensing, e.g., intraocular pressure or intracranial pressure (ICP), and more than two orders smaller than commercial solutions. The level of scaling may be achieved by leveraging the presented GDD detection scheme, which overcomes the operating frequency limits of traditional strategies and exhibits insensitivity to lossy tissue environments. This system may be used to capture human pulse waveforms in real time as well as to continuously monitor in vivo ICPs with sensors down to 2.5×2.5>0.1 mm$^3$. Furthermore, printable wireless sensor arrays may be used in concurrent spatial pressure mapping. The pressure sensor design allows ultra-thin and ultra-small flexible sensors, as well as a readout scheme.

The sensor design and detection scheme allow for a highly size-scalable system of pressure sensors with a wireless detection platform. Systematic design and tuning of these sensors by inductive spiral length may be determined with an analytical model, which is shown to agree with simulated and measured results. The greatest deviation between analytical calculations, electromagnetic simulations and measured resonant frequencies is observed with the smallest sensor. This is probably due to an overestimation of inductances at high spiral fill ratio by analytical models. Effective spiral length is desirable for improved mutual coupling to the readout antenna in the near field. This relationship is analogous to that of the number of inductor turns to mutual inductance in a transformer. However, the benefit of increasing effective spiral length is diminishing as thinner and more tightly spaced spirals are fit into a given area because parasitic resistances and capacitances become considerable. The 0.1 mm$^3$ device is designed with five turns, which is the maximum achievable in a 1-mm$^2$ area with a minimum feature size and pitch of 25 mm. The square design is later modified to remove edges and create a more rounded form factor for comfort and ease of implantation in human pulse waveform and in vivo mouse ICP studies.

The sensor system may operate with 44 mm$^2$ sensors over a distance of 15 mm in air from the readout antenna, while the smallest 11 mm$^2$ sensors operate over about 3 mm. The use of a micro structured elastomer as the dielectric layer enhances pressure sensitivity in the low pressure range due to an increase in effective permittivity on top of the reduction in separation distance between the spiral layers under compression. The 5-turn 11 mm$^2$ design with 50 mm metal traces and spacing outperforms the most sensitive passive wireless pressure. At pressures above 100 mm Hg, the microstructures are fully deformed and, hence, only the separation distance reductions act to increase the variable capacitance under applied pressure, resulting in a lower sensitivity. High Pearson correlation coefficient of 0.99 for the relationship between applied pressure and measured sensor resonant frequency indicates excellent linearity within the 0-100 mm Hg range. This is sufficient for the purposes of critical care and health monitoring, as physiological pressures fall within this range.

A further embodiment of active wireless sensing includes a battery-powered intraocular pressure monitor that is able to integrate into 1 cubic millimeter volume. The compact form has been achieved by vertically assembling two IC chips, a solar cell, battery and microelectromechanical system capacitive sensor. The wireless sensor has been shown to capture pressures every 15 min with a pressure resolution of 0.5 mmHg in bench top testing, through 5 mm of saline. The device memory can store pressure measurements up to 3 days before requiring an external wireless download. The device battery has a 28-day lifetime without recharging by the integrated solar cell.

Flexible sensor arrays perform additional application of wireless spatial pressure mapping for intracranial pressure. ICP mapping may be useful in assessing local pressure buildups. Moreover, multiple pressure sensors would allow flow rates to be determined from measured pressure differentials. Determining flow rate is important for cerebrospinal fluid shunt applications in patients with hydrocephalus. The flow rate can be used in a feedback loop to control the shunt valve opening and closing. Each 22 mm$^2$ pressure sensor in the prototype planar array is tuned with our analytical models to possess an individually addressable resonant frequency band spaced 350 MHz apart. For a typical pressure sensor with 1 MHz per mm Hg sensitivity, each sensor only needs to occupy a bandwidth of 100 MHz to cover the physiological pressure range of 0-100 mm Hg. This allows all sensors to be concurrently monitored with a single readout antenna. Unique resonant peaks corresponding to individual sensors in the array can be best distinguished in the GDD spectrum. Resonant peaks in the GDD spectrum are sharper than in the PRD spectrum for a sensor of the same quality factor, resulting in less overlap between frequency adjacent sensors. Non-uniform spacing of resonant frequencies and inconsistent pressure sensitivity of the fabricated sensor array can be primarily attributed to process variation. See, e.g., Chen et al., *Nature Communications*, 5: 5028, 2014; DOI: 10.1038/ncomms6028, which is incorporated herein by reference.

Optimizing Dialysate Flow Rate Through the Device Including a Multilayer Membrane The device including a multilayer membrane may have a diffusive clearance dependent upon blood and dialysate flow rates and the overall mass transfer area coefficient ($K_0A$) of the dialyzer. Although $K_0A$ should be constant for a given dialyzer, urea $K_0A$ has been reported to vary with dialysate flow rate possibly because of improvements in flow distribution. One may determine the dependence of $K_0A$ for urea, phosphate and β2-microglobulin on dialysate flow rate in dialyzers containing undulating fibers to promote flow distribution and two different fiber packing densities.

Clearances of urea and phosphate, but not β2-microglobulin, increased significantly with increasing dialysate flow rate. However, increasing dialysate flow rate had no significant effect on $K_0A$ or $K_0$ for any of the three solutes examined, although $K_0$ for urea and phosphate increased significantly as the average flow velocity in the dialysate compartment increased.

For dialyzers with features that promote good dialysate flow distribution, increasing dialysate flow rate beyond 600 mL/min at a blood flow rate of 400 mL/min is likely to have only a modest impact on dialyzer performance, limited to the theoretical increase predicted for a constant $K_0A$. See, e.g., Bhimani et al., *Nephrol Dial Transplant* 25: 3990-3995, 2010, which is incorporated herein by reference.

Device Including a Biosensor to Monitor Urea Levels in a Tissue of the Subject

The device including a multilayer membrane may include a biosensor to monitor urea levels in a tissue of the subject. The amperometric biosensor for urea determination measures a decomposition product of urea produced by urease which is an electrochemically oxidized. The carbon black (CB) paste electrode is covered by a semipermeable membrane containing immobilized urease. The urea biosensor action is based upon a cation-radical of the carbamic acid that undergoes dimerization to hydrazine. In addition, higher potential (>0.6 V), electro-oxidation of ammonia and amination of the electrode surface are observed. The working potential of 0.35 V may be selected for optimal urease-CB electrode operation, and the response properties of the electrode may be characterized. The biosensor possesses a linear range of response up to 5 mM of urea, a coefficient of variation equaling 3.7%, and a response time of 1.5 min. See, e.g., Laurinavicius, et al., *IEEE Sensors Journal*, 13: 2208-2213, 2013, which is incorporated herein by reference.

Device Including a Biosensor to Monitor Creatinine Levels in a Tissue of the Subject The device including a multilayer membrane may include a highly sensitive and stable conductometric biosensor for creatinine determination. Creatinine can be used for the diagnosis of renal, thyroid and muscle function. The biosensor is based on solid-state contact ammonium-sensitive sensor. Creatininase is chemically immobilized on the surface of the solid-state contact ammonium-sensitive membrane via glutaraldehyde covalent attachment method. The conductometric creatinine biosensors demonstrate high sensitivity and short response time toward creatinine. The detection limit of the biosensor was about $2 \times 10^{-6}$ M and the response time was shorter than 10 seconds in phophate buffer solution at pH 7.20. The linear dynamic range of the biosensor was between $1 \times 10^{-1}$ and $9 \times 10^{-6}$ M creatinine concentration in phosphate buffer solution at pH 7.2. The biosensor exhibited good operational and storage stability for at least 4 weeks kept in dry at 4-6° C. It had a reproducible and stable response during continuous work at least for 10 h with the relative standard deviation of 0.5% (n=48) for creatinine of $1 \times 10^{-3}$ M in phosphate buffer solution.

Creatinine is the end product of creatinine metabolism in mammalian cells. Therefore, it is an important diagnostic substance in biological fluid. Creatinine can be used for the diagnosis of renal, thyroid and muscle function. The creatinine level in blood serum and urine is clinically used as a parameter of muscle damage. The physiological concentration of creatinine ranges between 40 and 150 µmol/L in serum, but pathological values due to muscle disorder or kidney dysfunction may rise to concentration higher than 1000 µmol/L.

For routine creatinine determinations in clinical laboratory, the most frequently used methods are the HPLC and spectrophotometric one based on the Jaffe reaction. Several enzymatic methods have been reported to increase specificity. For this reason, the methods based on a combination of enzyme with specific sensor, such as ion-selective electrodes or other probes have been shown to be rapid, simple and promising for reduction of time and cost for the creatinine analysis. Various potentiometric and amperometric enzyme electrodes for creatinine determination have been reported. In these studies, a creatinine biosensor in a flow injection analysis system, and the application of a creatinine sensitive ion-selective field-effect transistor (ISFET) were described.

A device including conductometric sensors for biosensing devices consists of a planar glass support with interdigitated gold electrode pairs on one surface in a planar configuration. The operation of the biosensor device is based on measurement of the bulk conductance of the sensitive membrane due to biochemical reaction in solution. Conductometric sensor transducers are considerably beneficial since construction in a single way, high compatibility, rugged and relatively inexpensive, and no need of any reference electrode. Conductometric biosensors have also been described in the detection of glucose, urea, uric acid, sucrose, and trypsin.

An alternative conductometric creatinine biosensor may be based on solid-state contact ammonium-sensitive sensor chip membrane. The main analytical characteristics of the biosensor, such as pH behavior, time of immobilization and the enzyme loading have been investigated with respect to the influence on sensitivity, limit of detection, dynamic range, response time, operation and storage stability. See, e.g., Isildak et al., *Biochemical Engineering Journal* 62: 34-38, 2012, which is incorporated herein by reference.

Prophetic Example 1

Device Including a Multilayer Membrane to Control Wound Drainage

A device to control the transport and disposal of fluids from surgical wounds, and chronic wounds (e.g., diabetic, bedsores, etc.) includes a multilayer membrane, a membrane cleaner, a moisture sensor, a controller, a peristaltic pump, an ultraviolet sterilization light and a filtrate receptacle. In this example the device is applied to the leg wound of a diabetic patient to control the moisture level of the wound and to avoid microbial infection. The device is attached externally to cover the wound, maintain sterility and control moisture by removing wound exudate fluids. The controller activates the pump and the multilayer membrane to remove exudate fluids in response to signals from the moisture sensor.

A device including a multilayer membrane to control wound drainage is shown in FIG. 1. A semi-rigid plastic cover encompasses the multilayer membrane and forms a manifold connecting the membrane compartments with the peristaltic pump and a fluid waste reservoir. A multilayer membrane with three membrane layers comprised of electroactive polymers covers the wound and is sealed on its periphery by a sealant which prevents leakage of air or fluids into or out of the wound site. The sealant is a polymerizable adhesive composition (see e.g., U.S. Patent Appl. 2008/0243082 by Goodman published Oct. 2, 2008 which is incorporated herein by reference). A device including a multilayer membrane with three layers is made from electroactive polymers which are responsive to the controller. For example, an electroactive membrane may be constructed by electrochemically depositing polypyrrole-para-toluene-sulfonate onto a PVDF substrate to create a membrane that selectively transports cations when a pulsed, square wave potential is applied to the membrane (see e.g., Price et al., *Synthetic Metals* 102: 1338-1341, 1999 which is incorporated herein by reference). Electroactive membranes with pores of preselected sizes in predetermined locations may be created with an etching process using ion beam technology (see e.g., U.S. Pat. No. 7,632,406 issued to Wilson et al. on Dec. 15, 2009 which is incorporated herein by reference). For example, polycarbonate membranes coated in gold, containing pores approximately 0.1 µm in diameter may be constructed with the pores aligned on adjacent membrane layers (see FIG. 2). Device circuitry including a battery is used to draw an electrical potential across each membrane layer (See FIG. 2). Electronic activation of the membranes controls the passage of fluid through the membranes. For example, membranes comprised of electroactive polymers can act as valves with pores approximately 0.1-5.0 µm in diameter that open or close depending on the oxidation state of the polymers (see e.g., U.S. Patent Pub. No. 2006/0138371 by Gamier published on Jun. 29, 2006 which is incorporated herein by reference). Each membrane layer is activated or deactivated in sequence to control the flow of fluid (e.g., wound exudate) through the membranes. For example, sequential opening and closing of membrane pores to prevent backflow of wound exudate and wound infections may be as follows (See FIG. 3):

1) membrane 1 is open; membrane 2 is closed; membrane 3 is closed;
2) membrane 1 is closed; membrane 2 is open; membrane 3 is closed;
3) membrane 1 is closed; membrane 2 is closed; membrane 3 is open;

In concert with opening and closing of the membranes a pump may be activated to actively draw wound exudate fluids through the membranes and into a collection reservoir.

A peristaltic pump is connected to the compartments adjacent to each membrane layer (see FIG. 1). Multiphase peristaltic pumps are described (see e.g., Jeong et al., *Sensors and Actuators A* 123-124: 453-458, 2005 and Shkolnikov et al., *Sensors and Actuators A* 160: 141-146, 2010 which are incorporated herein by reference). Fluid flow through the multilayer membranes may be passive or active (i.e., peristaltic pumping). Active pumping from each membrane compartment is coordinated by the controller to coincide with opening and closing of the membrane pores as described above (see FIG. 3). The controller receives signals from a moisture sensor located in the wound site, and when excessive fluid accumulates the controller responds by initiating fluid transport through the multilayer membrane. A flexible sterile moisture sensor is incorporated in the device including a multilayer membrane to detect the level of exudate in the wound and to signal the controller. See e.g., McColl et al., *Wounds UK* 5: 94-99, 2009 which is incorporated herein by reference. Fluids are transported through the multilayer membrane and collected in a reservoir (see FIG. 1). The rate of exudate fluid accumulation in the reservoir and the moisture level in the wound are recorded by the controller and analyzed by the device circuitry. Methods to evaluate wound healing based on exudate fluids and wound moisture level are described. See e.g., White and Cutting, *Modern Exudate Management: A Review of Wound Treatments*, 2006; available online at: http://www.worldwidewounds.com/2006/september/White/Modern-Exudate-Mgt.html and McColl et al., Ibid. which are incorporated herein by reference.

The device including a multilayer membrane includes an ultraviolet (UV) light source to sterilize the multilayer membrane. For example, light emitting diodes (LED) that emit UV-C wavelength light are used for disinfection. An LED that emits approximately 254 nm wavelength light is available from Crystal IS, Inc., Green Island, N.Y. (e.g., see the Crystal IS-Technical Sheet which is incorporated herein by reference). Periodic exposure of the multilayer membranes to approximately 2000 to 8000 microwatt seconds per square centimeter of 254 nm light kills 90% of bacteria and viruses.

Prophetic Example 2

Device Including a Multilayer Membrane to Control Drainage of Cerebral Spinal Fluid A device including a multilayer membrane is used to control the flow of cerebral spinal fluid (CSF) in a patient with hydrocephalus. A cerebral shunt composed of a ventricular catheter, a distal catheter and the device including a multilayer membrane with a pressure sensor is implanted to control intracranial pressure in the patient. See FIG. 4. The flow of CSF fluid from the lateral ventricle of the brain to the peritoneal cavity is controlled by the multilayer membrane in the device which monitors intracranial pressure and responsively adjusts the fluid flow rate.

A device including a multilayer membrane is constructed with multilayer membranes, a pressure sensor and circuitry to control the flow of CSF in a ventricular-peritoneal shunt. The device including a multilayer membrane contains a three layer membrane with moveable membrane layers to control the flow of CSF. Membranes with pores of preselected sizes in predetermined locations may be created with an etching process using ion beam technology (see e.g., U.S. Pat. No. 7,632,406 issued to Wilson et al. on Dec. 15, 2009 which is incorporated herein by reference). For example, polycarbonate membranes, containing pores approximately 5.0 µm in diameter may be aligned to allow fluid to flow (see FIG. 5A) and misaligned to decrease fluid flow (see FIG. 5B). Membranes with pores approximately 0.1-5.0 in diameter which control fluid flow are described (see e.g., U.S. Patent Pub. No. 2006/0138371 by Gamier published on Jun. 29, 2006 which is incorporated herein by reference). The multilayer membranes may include different sized pores which can be selectively aligned to control fluid flow. For example, lateral movement of the membranes can align membrane pores that are 5.0 µm in diameter and misalign 0.1 µm pores to increase flow through the membrane (see FIG. 5C). Movement of the membrane layers is accomplished by piezo linear actuators. Piezo linear actuators with a maximum displacement of 2.2 µm and resolution to less than 1.0 nm are available from PI Ceramic GmbH, Lederhose, Germany (see e.g., Piezo Technical Sheet from PI Ceramics). Moreover, systems for membrane position control have been described (see e.g., U.S. Pat. No. 6,724,130 issued to Su et al, on Apr. 20, 2004 which is incorporated herein by reference).

A pressure sensor on the device including a multilayer membrane monitors intracranial pressure and signals to control circuitry on the device. For example, a passive resonant sensor to monitor intracranial pressure and signal wirelessly to control circuitry is described (see e.g., Chen et al., *Nature Communications* 5: 5028, 2014; DOI: 10.1038/ncomms6028 which is incorporated herein by reference). Control circuitry on the device including a multilayer membrane analyzes intracranial pressure readings and responds by moving multilayer membranes laterally to align or misalign different membrane pores (see FIG. 5C). Alignment of membrane pores may increase or decrease the flow rate of CSF through the cerebral shunt and decrease or increase intracranial pressure. Pressures ranging from 0-100 mm Hg are detected by the sensor and analyzed by the device controller. For example, if abnormally high intracranial pressure, e.g., approximately 30 mm Hg, is detected by the pressure sensor the control circuitry will move the membranes to align large pores (e.g. 5 µm pores) and relieve the pressure by allowing increased flow of CSF out of the lateral ventricle and into the peritoneal cavity. When normal intracranial pressure (e.g., approximately 7-15 mm Hg) is restored the controller may move the membranes to align smaller pores and reduce the flow rate of CSF from the brain to the peritoneal cavity. Continuous monitoring of intracranial pressure and adjustment of CSF flow rate is automated by programming the device including a multilayer membrane. The device may be implanted for days, weeks or longer to control intracranial pressure. The device is periodically sterilized by UV irradiation to prevent infection of the membranes, catheters and pressure sensor.

The device including a multilayer membrane includes an ultraviolet (UV) light source to sterilize the multilayer membranes and catheters. For example, light emitting diodes (LEDs) that emit UV-C wavelength light are used for disinfection. An LED that emits approximately 254 nm wavelength light is available from Crystal IS, Inc., Green Island, N.Y. (e.g., see the Crystal IS-Technical Sheet which is incorporated herein by reference). Periodic exposure of the multilayer membranes and attached catheters to approximately 2000 to 8000 microwatt seconds per square centimeter of 254 nm light kills 90% of bacteria and viruses. Irradiation down the lumen of catheters and on the faces of the multilayer membrane on a weekly schedule may prevent infection by microbes.

Prophetic Example 3

Device Including a Multilayer Membrane for Hemodialysis

A device including a multilayer membrane is used to remove waste products and excess water from the blood of a patient with kidney failure. A hemodialysis multilayer membrane device has multiple membrane layers composed of electroactive polymers which control metabolite diffusion and free water flow from the blood to the dialysate fluid. The device including a multilayer membrane contains sensors to detect the level of toxic metabolites in the blood of the patient, and control circuitry in the device responds to signals from the sensors by activating and deactivating the multilayer membranes in sequence. The device including a multilayer membrane has a sterilization unit to allow repeated hemodialysis with the same device.

A device including a multilayer membrane for hemodialysis is constructed with multilayer membranes that are responsive to electrical signals from the control circuitry of the device. A multilayer membrane with three membrane layers comprised of electroactive polymers is constructed with pores that allow passage of metabolites (e.g., urea, creatinine, phosphate and potassium ions), small proteins (e.g., $\beta_2$-microglobulin, cystostatin C, and myoglobin) and free water from the blood into a buffer solution (e.g., bicarbonate buffer). A multilayer membrane with a surface area of approximately 1.0 square meter is contacted on one side by arterial blood and on the opposite side by a dialysis solution (e.g., a sodium bicarbonate buffer solution which contains sodium and chloride at concentrations equivalent to those in normal plasma, and a normal blood pH (e.g., approximately pH 7.4). Counter-current flow, with blood flowing one direction on one side of the membrane and dialysis buffer flowing the opposite direction on the other side of the membrane promotes dialysis of the blood. A multilayer membrane with three layers is made from electroactive polymers which are responsive to the controller. For example, an electroactive membrane may be constructed by electrochemically depositing polypyrrole-para-toluenesulfonate onto a PVDF substrate to create a membrane that selectively transports cations when a pulsed, square wave potential is applied to the membrane (see e.g., Price et al., *Synthetic Metals* 102: 1338-1341, 1999 which is incorporated herein by reference). Electroactive membranes with pores of preselected sizes may be created with an etching process using ion beam technology (see e.g., U.S. Pat. No. 7,632,406 issued to Wilson et al. on Dec. 15, 2009 which is incorporated herein by reference). For example, polycarbonate membranes coated in gold, containing pores approximately 0.1 µm in diameter may be constructed with the pores aligned on adjacent membrane layers (see FIG. 2). Device circuitry including a battery is used to draw an electrical potential across each membrane layer (See FIG. 2). Electronic activation of the membranes controls the passage of fluid and metabolites through the membranes. For example, membranes comprised of electroactive polymers can act as valves with pores approximately 0.1-5.0 µm in diameter that open or close depending on the oxidation state of the polymers (see e.g., U.S. Patent Pub. No. 2006/0138371 by Gamier published on Jun. 29, 2006 which is incorporated herein by reference). Each membrane layer is activated or deactivated in sequence to control the flow of fluid (e.g., $H_2O$) through the membranes and to facilitate diffusion. For example, sequential opening and closing of membrane pores to promote diffusion and to prevent backflow of metabolites, toxins and water may be as follows (See FIG. 3):

1) membrane 1 is open; membrane 2 is closed; membrane 3 is closed;

2) membrane 1 is closed; membrane 2 is open; membrane 3 is closed;

3) membrane 1 is closed; membrane 2 is closed; membrane 3 is open;

Opening and closing of the membranes occurs as pumps continuously draw blood and dialysate past the multilayer membranes. For example the arterial blood flow rate may be approximately 400 mL/minute and the dialysate flow rate may be approximately 600 mL/minute to achieve optimal clearance of urea and phosphate from the blood (see e.g., Bhimani et al., *Nephrol. Dial. Transplant* 25: 3990-3995, 2010 which is incorporated herein by reference).

To monitor hemodialysis, sensors measure metabolites in the patient's blood and report the data to control circuitry on the device. For example an amperometric biosensor for urea samples the arterial blood entering the device including a multilayer membrane and reports the concentration of urea before, during and after hemodialysis. An amperometric biosensor for urea is described (see e.g., Laurinavicius et al., *IEEE Sensors Journal* 13: 2208-2213, 2013 which is incorporated herein by reference). Flow-through conductivity sensors monitor the ionic strength (e.g., Na+, K+, Cl−, HPO4− concentrations) of the dialysis fluid and the arterial blood entering the device including a multilayer membrane. Conductivity sensors that report to control microcircuitry are available from GE Healthcare Bio-Sciences AB, Uppsala, Sweden (see e.g., GE Conductivity Sensor Spec available online at: http://www.gelifesciences.com which is incorporated herein by reference). Also a creatinine biosensor is incorporated to monitor creatinine concentrations in the blood and dialysate. A conductometric creatinine biosensor which signals to microcircuitry is described (see e.g., Isildak et al., *Biochemical Engineering Journal* 62: 34-38, 2012 which is incorporated herein by reference). Metabolite concentration data and conductivity data are analyzed by microcircuitry in the device including a multilayer membrane which responds by opening or closing membrane pores and coordinated pumping of blood and dialysis fluid. The device including a multilayer membrane may also signal the patient or caregiver when dialysis is complete, for example, when urea and creatinine levels are within the normal range.

Each recited range includes all combinations and sub-combinations of ranges, as well as specific numerals contained therein.

All publications and patent applications cited in this specification are herein incorporated by reference to the extent not inconsistent with the description herein and for all purposes as if each individual publication or patent application were specifically and individually indicated to be incorporated by reference for all purposes.

Those having ordinary skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having ordinary skill in the art will recognize that there are various vehicles by which processes and/or systems and/or other technologies disclosed herein can be effected (e.g., hardware, software, and/or firmware), and that the preferred vehicle will vary with the context in which the processes and/or systems and/or other technologies are deployed. For example, if a surgeon determines that speed and accuracy are paramount, the surgeon may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies disclosed herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those having ordinary skill in the art will recognize that optical aspects of implementations will typically employ optically-oriented hardware, software, and or firmware.

In a general sense the various aspects disclosed herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices disclosed herein, or a microdigital processing unit configured by a computer program which at least partially carries out processes and/or devices disclosed herein), electrical circuitry forming a memory device (e.g., forms of random access memory), and/or electrical circuitry forming a communications device (e.g., a modem, communications switch, or optical-electrical equipment). The subject matter disclosed herein may be implemented in an analog or digital fashion or some combination thereof.

At least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

The herein described components (e.g., steps), devices, and objects and the description accompanying them are used as examples for the sake of conceptual clarity and that various configuration modifications using the disclosure provided herein are within the skill of those in the art. Consequently, as used herein, the specific examples set forth and the accompanying description are intended to be representative of their more general classes. In general, use of any specific example herein is also intended to be representative of its class, and the non-inclusion of such specific components (e.g., steps), devices, and objects herein should not be taken as indicating that limitation is desired.

With respect to the use of substantially any plural or singular terms herein, the reader can translate from the plural to the singular or from the singular to the plural as is appropriate to the context or application. The various singular/plural permutations are not expressly set forth herein for sake of clarity.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable or physically interacting components or wirelessly interactable or wirelessly interacting components or logically interacting or logically interactable components.

While particular aspects of the present subject matter described herein have been shown and described, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an"; the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A device comprising:
   a multilayer membrane including a plurality of layers, each layer of the plurality of layers having a plurality of variably-sized pores;
   an electroactive polymer within the each layer and surrounding each of the plurality of variably-sized pores; and
   a controller operably connected to sequentially activate the electroactive polymer to alter one or more sizes of the plurality of the variably-sized pores within a first layer of the multilayer membrane and to sequentially alter one or more sizes of the variably-sized pores sequentially within a second layer and one or more subsequent layers of the multilayer membrane;
   wherein at least one of the plurality of the variably-sized pores in the first layer is aligned with at least one of the plurality of variably-sized pores in one or more subsequent layers of the multilayer membrane.

2. The device of claim 1, wherein the controller sequentially activates the electroactive polymer to vary aperture of one or more of the plurality of the variably-sized pores and to vary accessibility to the one or more of the plurality of the variably-sized pores within the multilayer membrane.

3. The device of claim 1, wherein the controller is responsive to a conditional stimulus.

4. The device of claim 3, wherein the at least one of the plurality of the variably-sized pores in the first layer aligned with the at least one of the plurality of variably-sized pores in one or more subsequent layers of the multilayer membrane are accessible to fluid flow through a plurality of layers of the multilayer membrane in response to the conditional stimulus.

5. The device of claim 1, wherein the controller is operably connected to activate the electroactive polymer in the plurality of layers of the multilayer membrane to produce peristaltic pumping activity by aligned variably-sized pores in three or more layers of the multilayer membrane.

6. The device of claim 1, wherein the controller is operably connected to activate the electroactive polymer in to provide variable fluid flow rates by separately controlling the size of one or more aligned variably-sized pores of each layer of two or more layers of the multilayer membrane.

7. The device of claim 1, wherein the controller is operably connected to activate the electroactive polymer to separately control movement of each layer of two or more layers to provide variable fluid flow rates.

8. The device of claim 1, comprising a pump configured to apply pressure or suction to the multilayer membrane.

9. The device of claim 8, wherein the controller is operably connected to alter the relative position of the two or more layers of the multilayered membranes to expose one or more of the plurality of variably-sized pores in each of the two or more layers to pressure or suction from the pump.

10. The device of claim 1, comprising one or more nanoporous layers in the multilayer membrane, wherein the controller is operably connected to activate the electroactive polymer in the one or more nanoporous layers to provide controlled transport of fluid through the one or more nanoporous layers.

11. A method of varying a fluid flow rate through a multilayer membrane comprising:
sending a control signal from a controller operably connected to activate an electroactive polymer within each layer of a plurality of layers of a multilayer membrane, wherein the electroactive polymer surrounds each of a plurality of variably-sized pores in the plurality of layers of the multilayer membrane;
altering the electroactive polymer surrounding one or more sizes of the plurality of variably-sized pores within a first layer of the multilayer membrane and altering the one or more sizes of the variably-sized pores sequentially within a second layer and one or more subsequent layers of the multilayer membrane; and
aligning at least one of the plurality of the variably-sized pores in the first layer with at least one of the plurality of variably-sized pores in one or more subsequent layers of the multilayer membrane.

12. The method of claim 11, comprising:
controlling accessibility to the one or more sizes of the plurality of the variably-sized pores within the multilayer membrane by altering the electroactive polymer in response to a conditional stimulus.

13. The method of claim 11, comprising: receiving a conditional stimulus at the controller.

14. The method of claim 13, comprising: aligning the at least one of the plurality of the variably-sized pores in the first layer with the at least one of the plurality of variably-sized pores in one or more subsequent layers of the multilayer membrane to provide access to fluid flow through a plurality of layers of the multilayer membrane in response to the conditional stimulus.

15. The method of claim 11, comprising: sending a control signal from the controller operably connected to activate the electroactive polymer in the plurality of layers of the multilayer membrane to produce peristaltic pumping activity by aligned variably-sized pores in three or more layers of the multilayer membrane.

16. The method of claim 15, comprising: sending a control signal from the controller operably connected to activate the electroactive polymer to alter the size of one or more aligned variably-sized pores sequentially for each layer of two or more layers of the multilayer membrane to generate pressure or suction through the multilayer membrane.

17. The method of claim 11, comprising: sending a control signal from the controller operably connected to activate the electroactive polymer to provide variable fluid flow rates by separately controlling the size of one or more aligned variably-sized pores of each layer of two or more layers of the multilayer membrane.

18. The method of claim 11, comprising: sending a control signal from the controller operably connected to activate the electroactive polymer to separately control movement of each layer of two or more layers to provide variable fluid flow rates.

19. The method of claim 11, comprising:
applying pressure or suction to the multilayer membrane through a pump.

20. The method of claim 19, comprising:
sending a control signal from the controller to alter the relative position of two or more layers of the multilayered membranes to expose the one or more of the plurality of variably-sized pores in each of the two or more layers to pressure or suction from the pump.

21. The method of claim 11, comprising:
sending a control signal from the controller to control fluid flow through each layer of the plurality of layers of the multilayer membrane by altering the electroactive polymer to push fluid flow or pull fluid flow through the multilayer membrane.

22. The method of claim 11, comprising:
sending a control signal from the controller to control fluid flow through each layer of the plurality of layers of the multilayer membrane by altering the electroactive polymer to provide pulsed transport to control entry rate and exit rate of fluid through the multilayered membrane.

23. The method of claim 11, comprising:
sending a control signal from the controller to control fluid flow through each layer of the plurality of layers of the multilayer membrane by altering the electroactive polymer to provide continuous transport to control entry rate and exit rate of fluid through the multilayered membrane.

24. The method of claim 11, comprising:
sending a control signal from the controller to alter the electroactive polymer in one or more nanoporous layers of the plurality of layers of the multilayer membrane to control flow through the one or more nanoporous layers.

25. The method of claim 11, comprising:
sending a control signal from the controller to a UV illumination source to activate self-sterilization of the device.

26. A device comprising:
a multilayer membrane including a plurality of layers, each layer of the plurality of layers having a plurality of pores on the plurality of layers of the multilayer membrane;
an actuator operably attached to the plurality of layers of the multilayer membrane; and
a controller operably activating the actuator to differentially actuate two or more of the layers to alter a relative lateral position of the two or more layers of the plurality of layers to align two or more of the plurality of pores within the two or more layers of the plurality of layers of the multilayer membrane;
wherein the two or more pores are aligned and accessible through the two or more layers of the plurality of layers of the multilayer membrane.

27. The device of claim 26, wherein two or more pores of the each layer of the plurality of layers have a substantially identical size.

28. The device of claim 26, wherein at least one pore of the each layer of the plurality of layers have a variable size.

29. The device of claim 28, wherein the controller is operably connected to the plurality of layers of the multilayer membrane to produce peristaltic pumping activity by aligned variably-sized pores in three or more layers of the multilayer membrane.

30. The device of claim 28, wherein the controller is operably connected to alter the size of at least one of the aligned variably-sized pores of each layer of the two or more layers to generate pressure or suction.

31. The device of claim 26, wherein the controller is operably connected to sequentially activate the actuator to vary accessibility to the two or more of the plurality of pores.

32. The device of claim 26, wherein the controller is responsive to a conditional stimulus.

33. The device of claim 26, wherein the plurality of pores includes pores of variable size and pores of fixed size.

34. The device of claim 26, wherein the controller operably activates the actuator to provide variable fluid flow rates by separately controlling lateral movement of each layer of the two or more layers.

35. The device of claim 34, comprising one or more nanoporous layers in the multilayer membrane, wherein the controller operably activates the actuator to open and close pores to provide controlled transport of fluid through the nanoporous layer.

36. A method of varying a fluid flow rate through a multilayer membrane comprising:
   sending a control signal from a controller operably connected to activate an actuator operably attached to a plurality of layers of the multilayer membrane to differentially actuate two or more of the layers to alter a relative lateral position of the two or more layers of the plurality of layers, wherein each layer of the plurality of layers has a plurality of pores on the plurality of layers; and
   aligning by the actuator two or more pores of the plurality of pores in the two or more layers of the multilayer membrane.

37. The method of claim 36, comprising:
   controlling accessibility to the two or more pores within the multilayer membrane by activating the actuator to align the two or more pores of the plurality of pores.

38. The method of claim 36, comprising: receiving a conditional stimulus at the controller.

39. The method of claim 36, comprising: sending a control signal from the controller to activate the actuator to alter the relative lateral position of three or more layers of the multilayer membrane to produce peristaltic pumping activity by aligned pores in the three or more layers.

40. The method of claim 36, comprising:
   applying pressure or suction to the multilayer membrane through a pump.

41. The method of claim 40, comprising:
   sending a control signal from the controller to alter the relative position of two or more layers of the multilayered membranes to expose the two or more pores to pressure or suction from the pump.

42. The method of claim 36, comprising:
   sending a control signal from the controller to control fluid flow through each layer of the two or more layers of the multilayer membrane by activating the actuator to push flow or pull flow through the multilayer membrane.

43. The method of claim 36, comprising:
   sending a control signal from the controller to control fluid flow through each layer of the two or more layers of the multilayer membrane by activating the actuator to provide pulsed transport to control entry rate and exit rate of fluid through the multilayered membrane.

44. The method of claim 36, comprising:
   sending a control signal from the controller to control fluid flow through each layer of the two or more layers of the multilayer membrane by activating the actuator to control continuous transport to control entry rate and exit rate of fluid through the multilayered membrane.

45. The method of claim 36, comprising:
   sending a control signal from the controller to control fluid flow through each layer of the two or more layers of the multilayer membrane by activating the actuator to control flow through one or more nanoporous layers in the multilayer membrane.

46. The method of claim 36, comprising:
   sending a control signal from the controller to a UV illumination source to activate self-sterilization of the device.

* * * * *